US006463801B1

United States Patent
Young et al.

(10) Patent No.: US 6,463,801 B1
(45) Date of Patent: Oct. 15, 2002

(54) APPARATUS, METHOD AND SYSTEM FOR MEASUREMENT OF SEA-FLOOR SOIL CHARACTERISTICS

(75) Inventors: Alan G. Young, Sugarland; Lowell Vaughan Babb, The Woodland, both of TX (US)

(73) Assignee: Marsco, Inc., Houston, TX (US)

( * ) Notice: Subject to any disclaimer, the term of this patent is extended or adjusted under 35 U.S.C. 154(b) by 0 days.

(21) Appl. No.: 09/204,418

(22) Filed: Dec. 2, 1998

(51) Int. Cl.[7] .................................. G01N 1/04
(52) U.S. Cl. ................................... 73/170.32
(58) Field of Search .................. 73/170.32, 84, 73/864.44, 864.45; 175/20, 58

(56) References Cited

U.S. PATENT DOCUMENTS

| | | | | |
|---|---|---|---|---|
| 2,384,739 A | * | 9/1945 | Hasbrook | 73/170.32 |
| 3,345,879 A | * | 10/1967 | Nasu et al. | 73/170.32 |
| 3,774,718 A | * | 11/1973 | Igarashi et al. | 73/170.32 |
| 3,940,982 A | * | 3/1976 | Hironaka | 73/170.32 |
| 3,965,728 A | * | 6/1976 | van den Berg | 73/84 |
| 4,166,508 A | * | 9/1979 | van den Berg | 175/20 |
| 4,530,236 A | * | 7/1985 | van den Berg | 175/162 |
| 4,806,049 A | * | 2/1989 | Cour | 405/161 |
| 5,050,424 A | * | 9/1991 | Anesa et al. | 73/1 D |
| 5,125,266 A | * | 6/1992 | Ingram et al. | 73/84 |
| 5,127,261 A | * | 7/1992 | Ingram et al. | 73/94 |
| 5,777,242 A | * | 7/1998 | Zuidberg et al. | 73/864.45 |
| 5,804,715 A | * | 9/1998 | Bennett | 73/170.32 |

* cited by examiner

*Primary Examiner*—Hezron Williams
*Assistant Examiner*—Nashmiya Fayyaz
(74) *Attorney, Agent, or Firm*—Alan H. Gordon & Associates, P.C.

(57) ABSTRACT

A system is presented with a seabed unit, a remotely operated vehicle (ROV), a cone rod measuring device, and a support ship. The seabed unit is lowered from the support ship by a winch line to the seafloor itself. A caisson on the seabed unit is used to secure the seabed unit to the seafloor. The ROV then inserts the cone rod measurement device into the upper thruster unit of the seabed unit. The thruster unit has a jacking mechanism for inserting the cone rod into the soil of the seafloor. The ROV has a hydraulic power source and hydraulic controls to manipulate the hydraulic actuators of the thruster unit to control the manner and timing of the jacking process that inserts and extracts the cone rod measuring unit into the seafloor. The ROV contains underwater cameras and control units that observe measurement gauges on the thruster unit and allow appropriate manipulation of the hydraulic controls on the ROV and the thruster unit. The ROV can contain telemetry devices to extract and transmit data obtained from the cone rod measuring unit, or the cone rod measuring unit can contain its own electronic packages to transmit the data immediately or to store the information for downloading up recovery by the support ship. Beside cone rod measuring units, the present invention can also employ coil rod measuring units and a wide variety of other measuring devices.

4 Claims, 12 Drawing Sheets

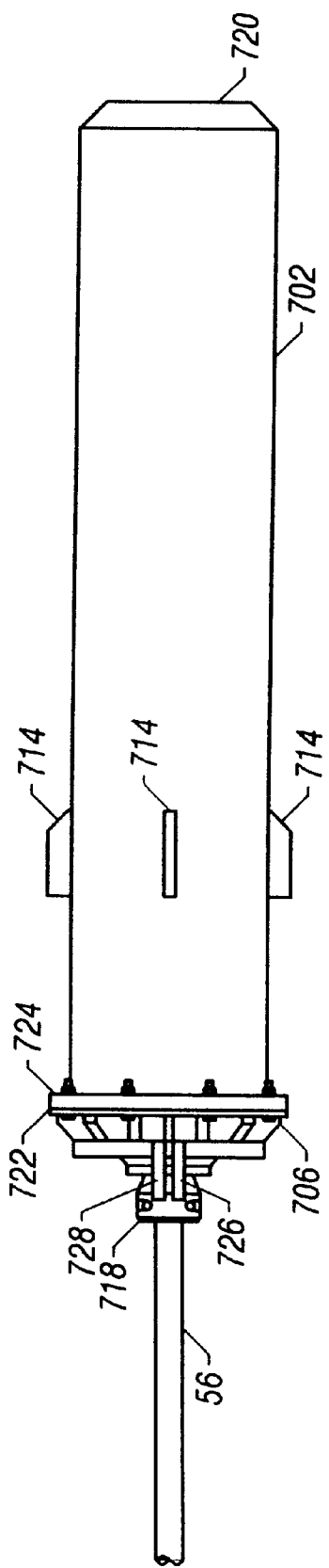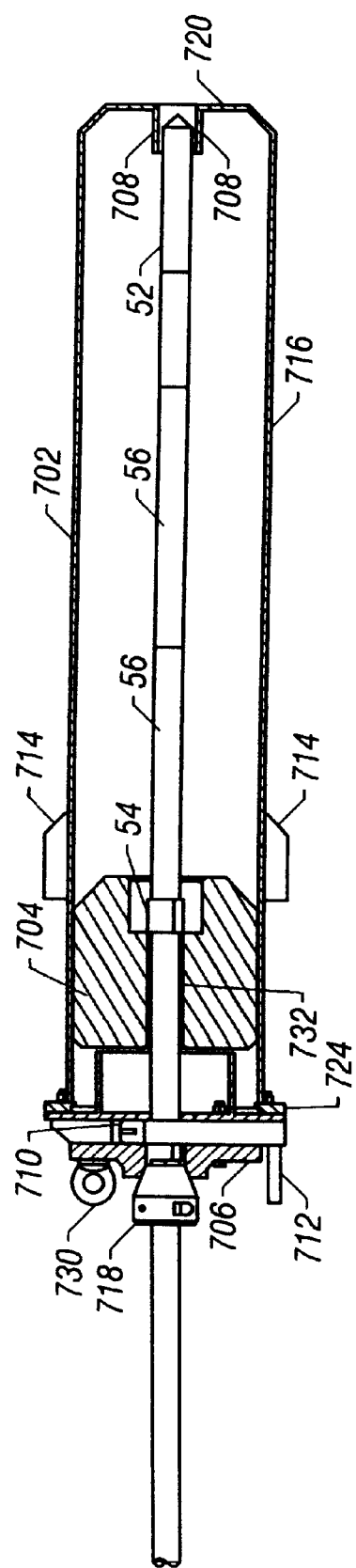

APPARATUS, METHOD AND SYSTEM FOR MEASUREMENT OF SEA-FLOOR SOIL CHARACTERISTICS

CROSS REFERENCE TO RELATED PATENT APPLICATION

There are no related applications.

BACKGROUND OF THE INVENTION

1. Field of the Invention

The present invention relates to a system for measuring the soil characteristics beneath the sea, and more particularly, in the placement of penetration devices to measure soil characteristics directly and to remove soil samples at the sea floor under deep water.

2. Description of the Related Technology

As land-based reserves of oil and natural gas have become more scarce or expensive to produce, oil companies have turned to offshore sources. Once precarious, offshore oil platform drilling is now commonplace and profitable. Consequently, oil companies have sought to extend the reach of offshore drilling into deeper water. Currently, the maximum depth for offshore rigs is roughly 8,000 feet, however more widespread deepwater drilling is desirable.

In order to secure platforms in deepwater, various techniques are used to secure anchors, such as continuous suction anchors, to the seafloor. Continuous suction anchors are relatively flat, hockey-puck shaped cylinders that are embedded into the seafloor. A suction pump is then attached to the anchor and water extracted from within the hollow caisson to generate a reaction against which a ship or floating platform may be attached. Unfortunately, continuous suction action is required in order to maintain the reaction as water seeps within the caisson from underneath the shallow walls of the caisson itself. This seepage varies with the type of soil in which the anchor is laid. Other types of anchors, namely plate anchors, also require information about the soil in which they are embedded. Consequently, in order to ensure proper anchoring, the soil of the anchor site must be tested. In some cases, the soil must be tested to a depth of 120 to 150 feet. In the prior art, the soil testing was accomplished by employing large ships, called drillships, to use drill pipe to reach the seafloor 8,000 or more feet below, so that the measuring cone could be implanted the additional 100 feet or more under the seafloor. Use of the large, expensive drillships, along with the crews and resources needed to construct the 5,000+feet of pipe needed, is very expensive and time consuming.

The alternatives to drillships in the prior art were large, heavy all-in-one apparatuses called a deadweight rig. The deadweight rig was lowered from a ship using a very heavyweight winch. As the name implies, the deadweight rig utilized a large dead weight, usually in the shape of a large hockey puck, that simply sat on the seafloor. The deadweight rig had its own internal hydraulic power system and associated control mechanism. The power and control for the deadweight rig, however, was supplied by the support ship through a large number of umbilical cords (called umbilicals). Unfortunately, the necessity for umbilicals has limited the utility of the deadweight rig, for the most part, to shallow water testing. Moreover the use of the deadweight, and the large amount of equipment for the rig carried on the deadweight, resulted in difficult and hazardous conditions on the support ship during deployment and recovery. Finally, all-in-one nature of the deadweight rig left little ability to cope with misfortune underwater.

There is, therefore, a need in the art for an apparatus and system for measuring seafloor soil characteristics without stringing 8,000 or more feet of drill pipe, without having to employ large ships with which to operate the drill tubing, and without the need to employ cumbersome deadweight seafloor templates.

SUMMARY OF THE INVENTION

The present invention solves the problems inherent in the prior art by providing an apparatus, system and method of measuring seafloor soil characteristics without requiring drill ships or thousands of feet of drill pipe.

The present invention is a deepwater suction caisson-based testing system. The present invention comprises a seabed unit, a support ship, and a remotely operated vehicle ("ROV"). The seabed unit has a removable thrusting unit atop a capped suction caisson foundation. The suction caisson provides the required reaction force for a cone penetrometer that is co-axially driven by the thrusting unit. The thrusting unit contains all the active components of the system, which includes a rod thruster drive unit, ROV mateable quick disconnect ports, and visual gauges. The ROV is equipped with a stab for interfacing both with the pump of the suction caisson and with the thruster drive unit. The ROV is capable of mating and de-mating while underwater.

The present invention comprises four units, a seabed unit, a remotely operated vehicle (ROV), the cone rod measuring device, and a support ship. The seabed unit is lowered from the support ship by a wireline winch to the seafloor. A caisson on the seabed unit is used to secure the seabed unit to the seafloor. The ROV then inserts the cone rod measurement device into the upper thruster unit of the seabed unit. The thruster unit has a jacking mechanism for inserting the cone rod into the soil of the seafloor. The ROV supplies the hydraulic power and hydraulic controls to the hydraulic actuators of the thruster unit to control the manner and timing of the jacking process that inserts and extracts the cone rod measuring unit into the seafloor. The ROV is itself controlled remotely by operators stationed on the support ship. The ROV contains underwater cameras and control units that observe measurement gauges on the thruster unit and manipulate the hydraulic controls of the ROV and the thruster unit. The ROV can contain telemetry devices to extract and transmit data obtained from the cone rod measuring unit, or the cone rod measuring unit can contain its own electronic packages that store the information for downloading upon recovery by the support ship. Beside cone rod measuring units, the present invention can also employ coiled rod thrusting unit as well as a wide variety of other measuring devices.

The suction caisson includes the floor, guide cylinder, stab attachments, surface sling attachments, and valve ports. The suction caisson comprises a rolled and welded steel assembly that is capped at one end and open at the other. The guide cylinder extends forty-eight inches from the closed end of the suction caisson assembly into a cylindrical shell, forming a coaxial assembly. The caisson structural supports are constructed and arranged to facilitate structural integrity and embedment into the seafloor.

The present invention is equipped with a ROV interface (stab) receptacle to make connections from the ROV to the seabed unit. The stab receptacle is attached to a thruster unit supporting leg in case emergency removal of the thrusting unit from the caisson is needed. The ROV interface stab has suitable hydraulic and water connections to establish connection with the thrusting unit and the caisson.

A seawater pump is attached either to the caisson, to the ROV, or to the jacking unit. The seawater pump has variable pressure settings that are actuated by the ROV. Control of the clamp and rod thruster assemblies is through auxiliary solenoid valves. The ROV utilizes primary hydraulics for the caisson. The main pump/suction line of the caisson is equipped with a breakaway feature, which allows recovery of the upper assembly in the event of an emergency or failure in the caisson.

The ROV is equipped with a mating interface plate that is utilized for interfacing with the caisson mounted stab receptacle. The ROV mounted stab will decouple from the host ROV after mating and, through a suitable flexible hose, allowing the ROV to travel a minimum of 10 feet away from the caisson while remaining coupled. This procedure allows the ROV to move around the seabed unit and observe various gauges and the various devices on the seabed unit while being able to manipulate hydraulic controls.

Other and further objects, features and advantages will be apparent from the following description of presently preferred embodiments of the invention, given for the purpose of disclosure and taken in conjunction with the accompanying drawings.

BRIEF DESCRIPTION OF THE DRAWINGS

FIG. 8 is a side view of an embodiment of the guide sleeve of the present invention;

FIG. 9 is a cross-sectional view of an embodiment of the guide sleeve of the present invention;

DETAILED DESCRIPTION OF THE PREFERRED EMBODIMENTS

The present invention is an apparatus, method and system for taking measurements and samples from the floor of the sea. The present invention allows soil measurements to be taken in very deep water, well in excess of 8,000 feet. Indeed, the present invention is limited only by the depth and power limitations of the ROV used.

Overview

Figure 1:
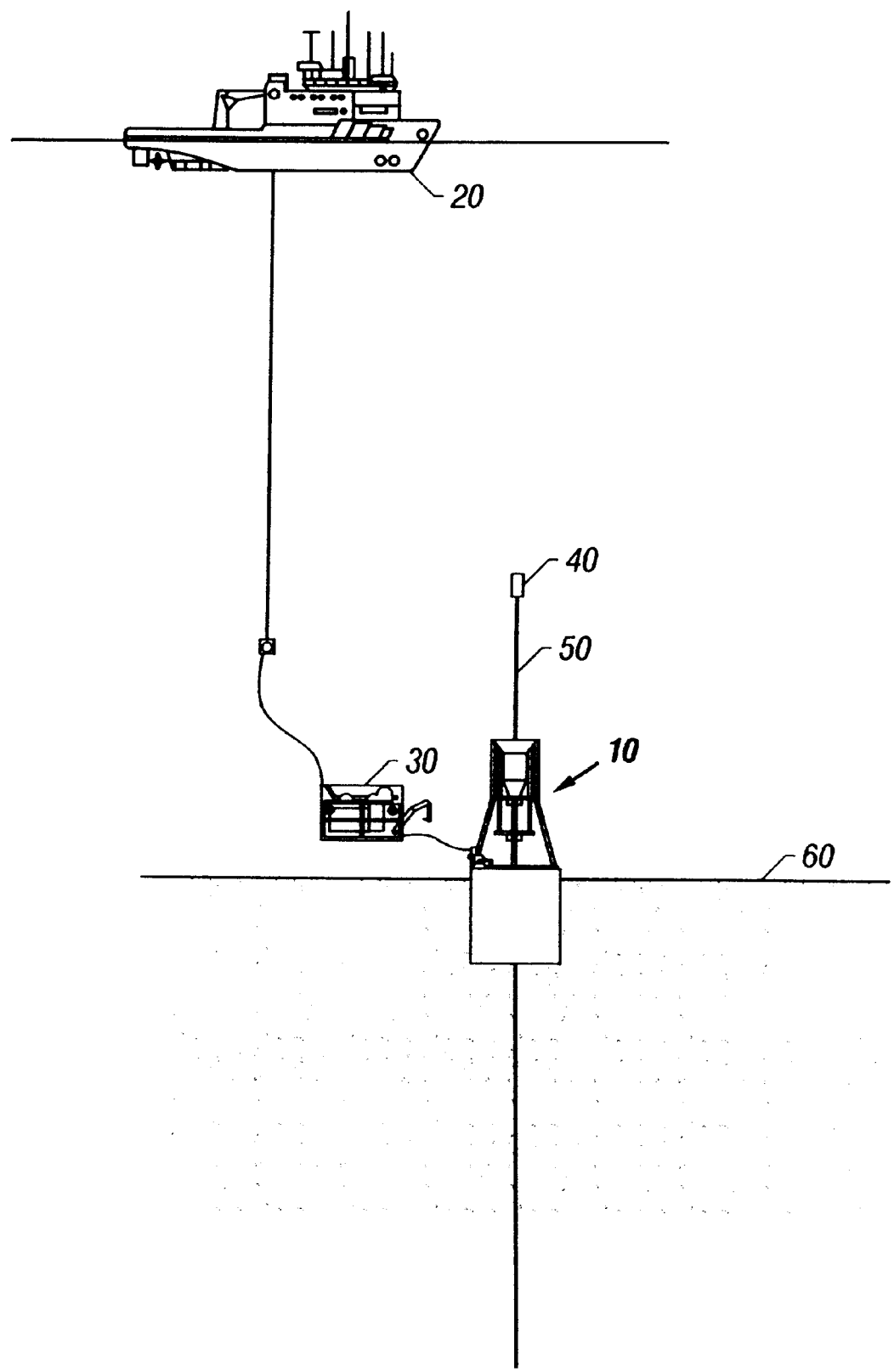
FIG. 1 is a schematic drawing of the present invention.
Figure 2:
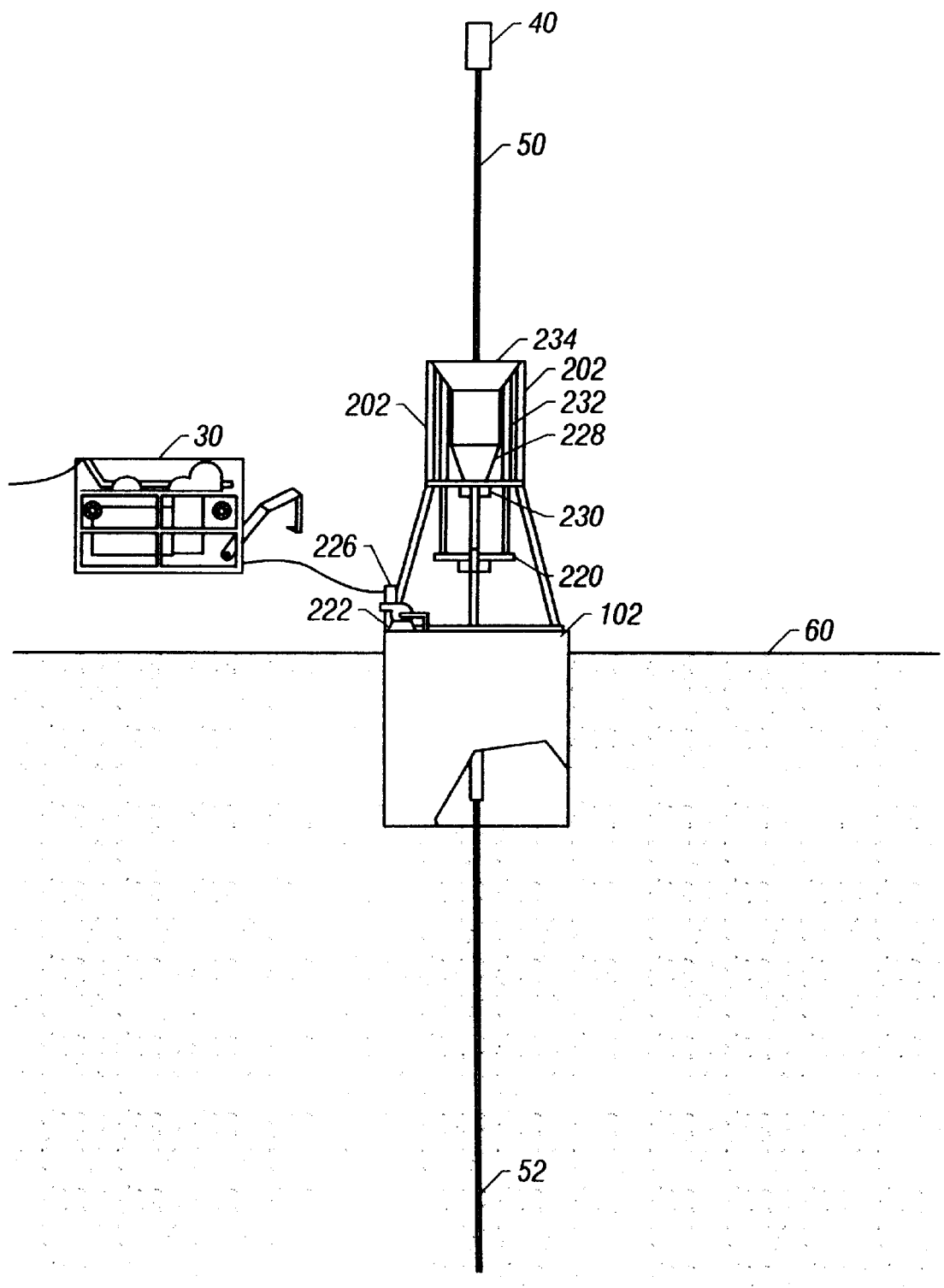
FIG. 2 is a side view of the seabed unit of one embodiment of the present invention.

The present invention is a deepwater suction caisson-based testing system. As shown in FIGS. 1 and 2, the present invention comprises a seabed unit 10, a support ship 20, and a remotely operated vehicle ("ROV") 30. The seabed unit 10 has an ROV removable thrusting unit 202 atop a capped suction caisson 102 foundation. The caisson 102 provides the required reaction force for a cone penetrometer that is co-axially driven into the seafloor by a thruster atop the caisson. The thrusting unit 202 contains all the moving components of the seabed unit 10, which includes a rod thruster drive unit, ROV mateable quick disconnect ports, and visual gauges. The ROV 30 is equipped with a stab for interfacing both with the pump 222 for the suction caisson 102 and with the thruster drive unit 202. The ROV 30 is capable of mating and de-mating while underwater.

The seabed unit 10 is lowered from the support ship 20 by a winch line to the seafloor 60. A caisson 102 on the seabed unit 10 is used to secure the seabed unit 10 to the seafloor 60. The ROV 30 then inserts the cone rod measurement device 50 into the upper thruster unit 202 of the seabed unit 10. The thruster unit 202 has a jacking mechanism for inserting the cone rod 50 into the soil underneath the seafloor 60. The ROV 30 supplies the hydraulic power and the hydraulic controls to the hydraulic actuators of the thruster unit 202 in order to control the manner and timing of the jacking process that inserts and extracts the cone rod measuring unit 50 into and out of the soil under the seafloor 60. The ROV 30 is itself controlled remotely by operators stationed on the support ship 20. The ROV 30 contains underwater cameras and control units that observe measurement gauges on the thruster unit 202 and manipulate the hydraulic controls of the ROV 30 and the thruster unit 202. The ROV 30 can contain telemetry devices to extract and transmit data obtained from the cone rod measuring unit 50, or the cone rod measuring unit 50 can contain its own electronic packages that store the information for downloading upon recovery by the support ship 20. Beside cone rod measuring units 50, the present invention can also employ coil rod thruster units and a wide variety of other measuring devices.

Figure 3:
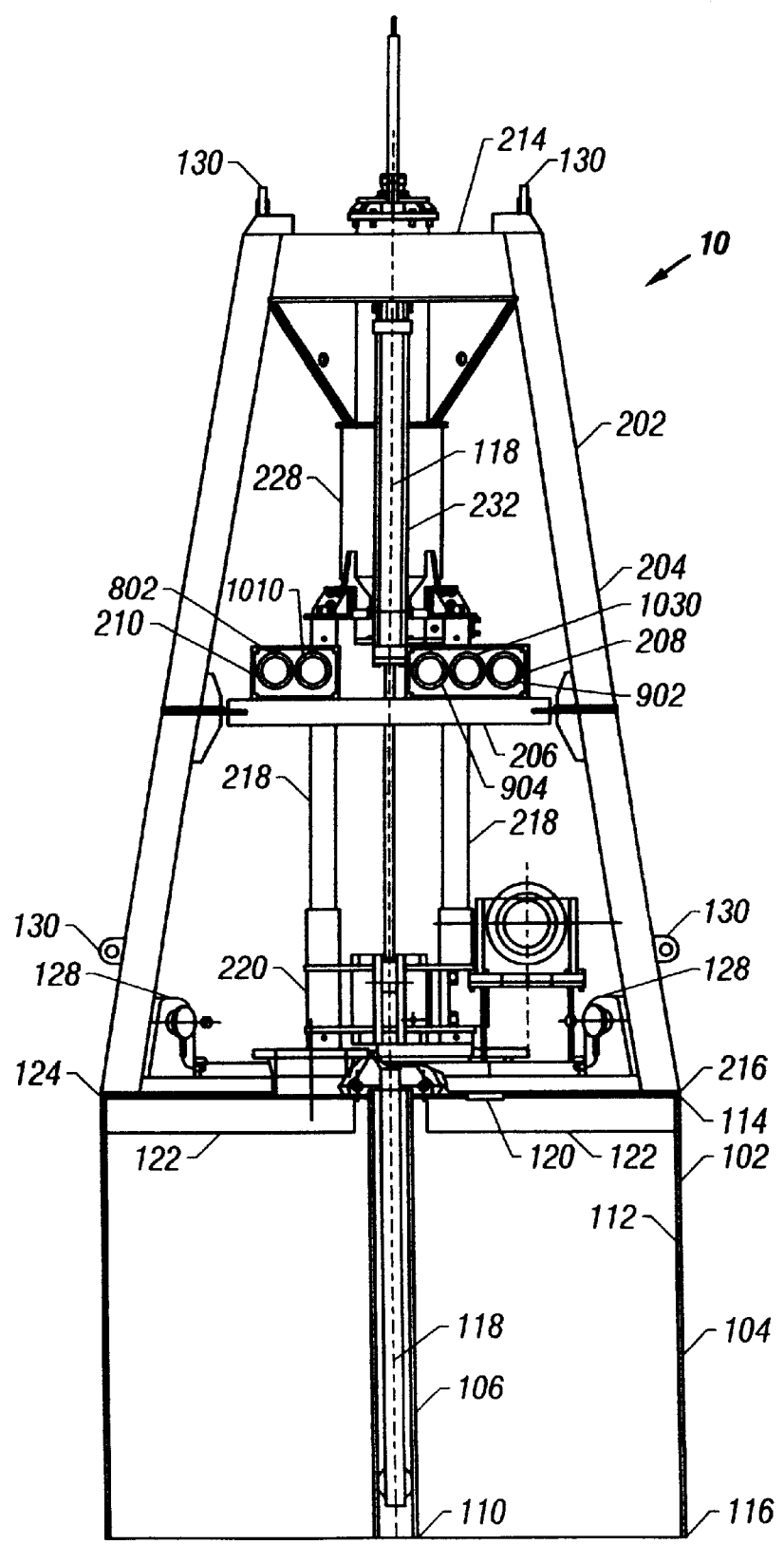
FIG. 3 is a side view of the preferred embodiment of the seabed unit of the present invention.
Figure 17:
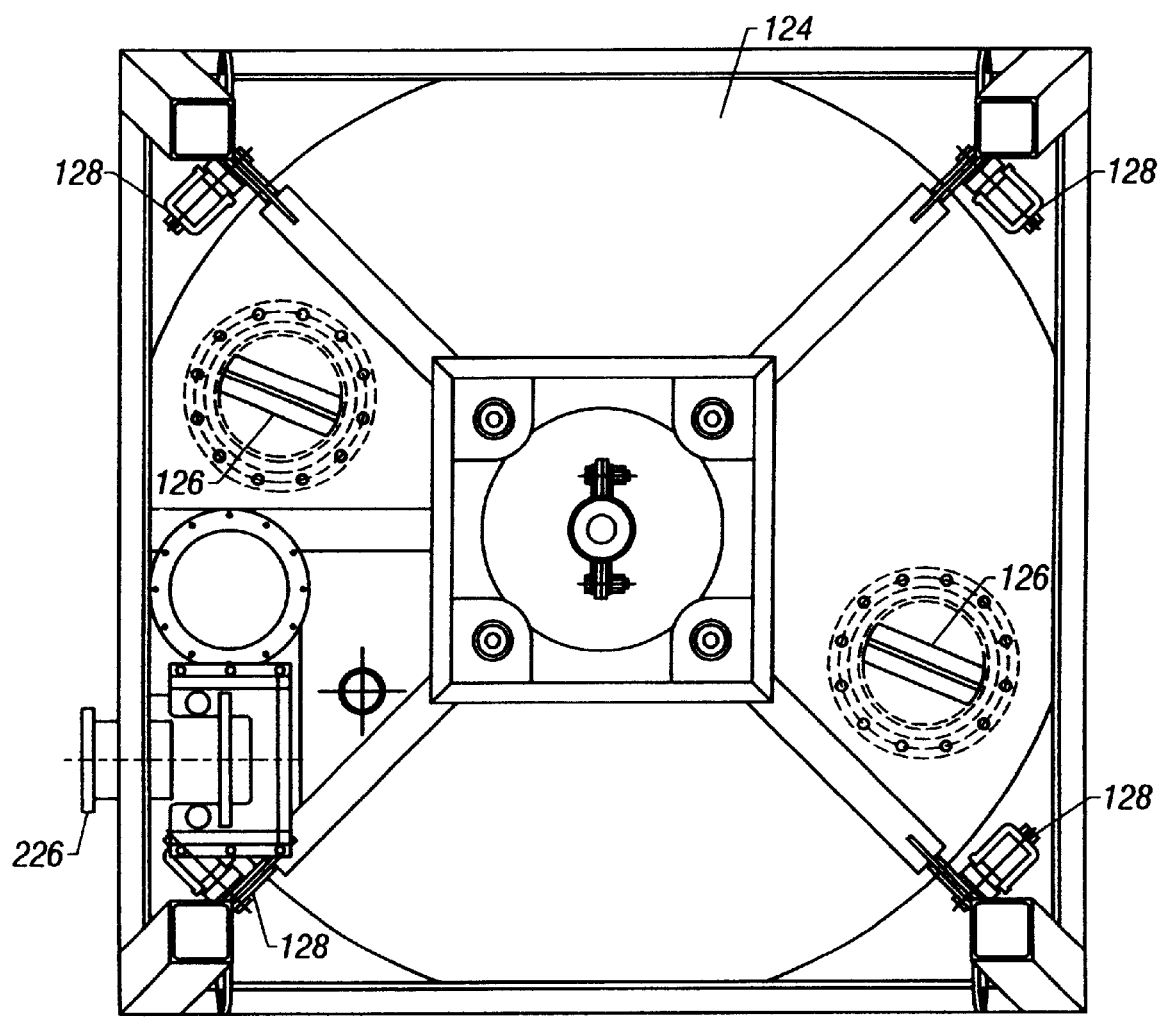
FIG. 17 is a top cross sectional view of the jacking unit and caisson of the present invention.

As shown in FIGS. 2 and 3, the suction caisson includes the floor 124 guide cylinder 106, stab attachments 226, surface sling attachments 130, and valve ports 126 (FIG. 17). The suction caisson consists of a rolled and welded steel assembly that is capped at one end and open at the other. The guide cylinder extends forty-eight inches from the closed end of the suction caisson assembly 102 into a cylindrical shell, forming a coaxial assembly. The caisson structural supports 122 are constructed and arranged to facilitate structural integrity and embedment into the seafloor.

The present invention is equipped with a ROV interface (stab) receptacle 226 to make connections from the ROV 30 to the seabed unit. The stab receptacle 226 is attached to a thruster unit supporting leg 204 in case emergency removal of the thrusting unit 202 from the caisson 102 is needed. The ROV 30 interface stab has suitable hydraulic and water connections to establish connection with the thrusting unit and the caisson 102.

Figure 14:
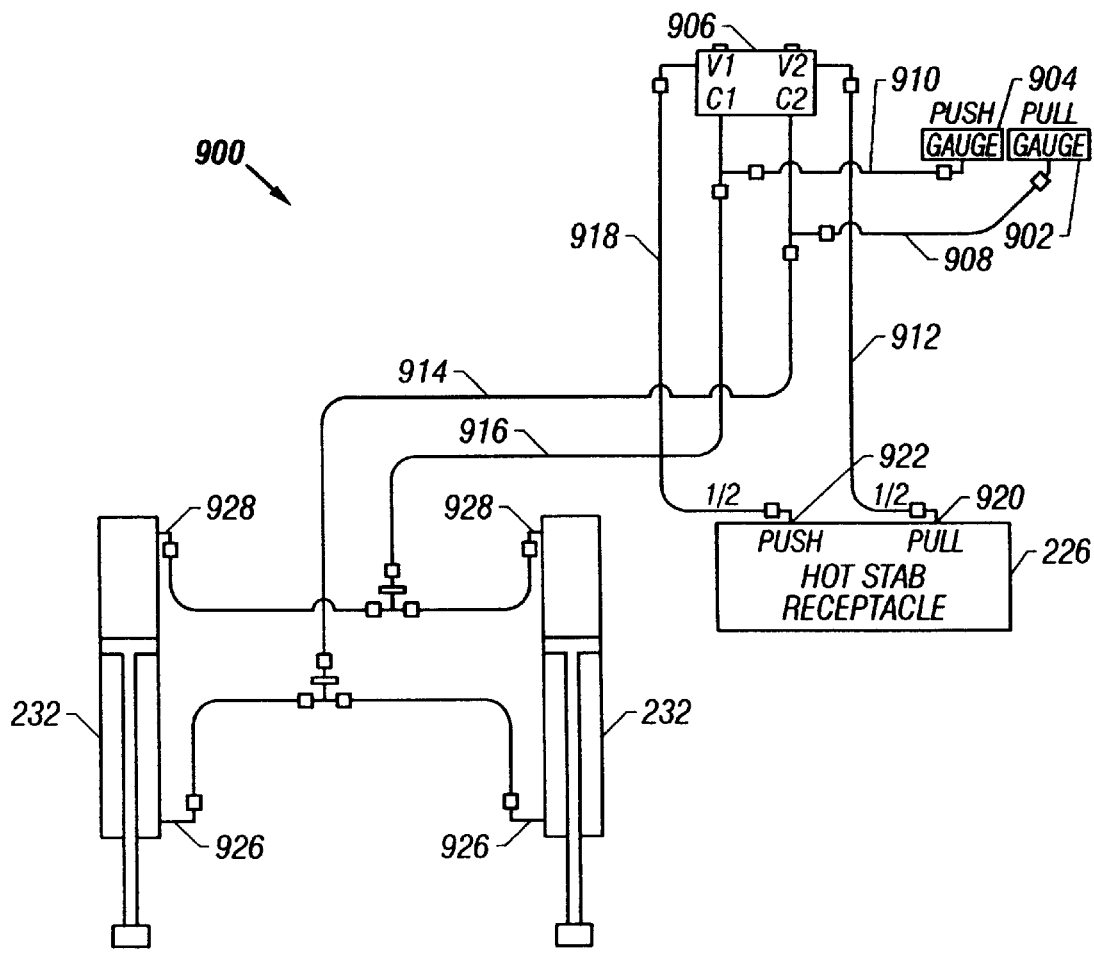
FIG. 14 is a schematic of the hydraulic system for the to the jacking actuators of the present invention.
Figure 15:
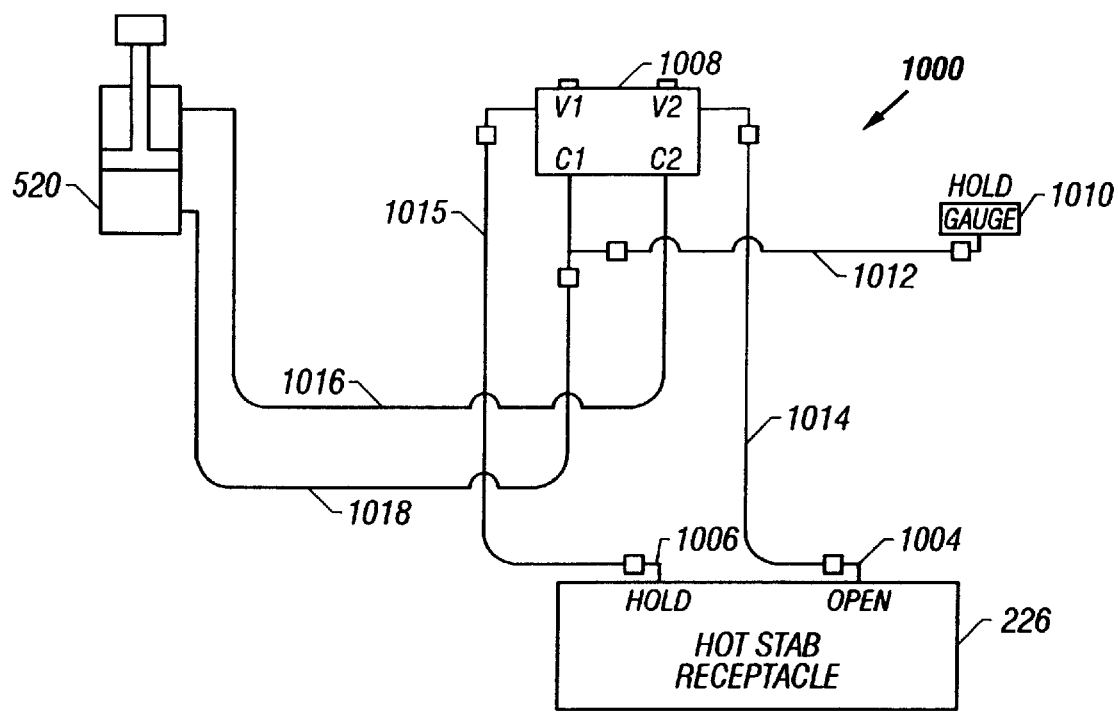
FIG. 15 is a schematic of the hydraulic system for the upper clamp of the present invention.
Figure 16:
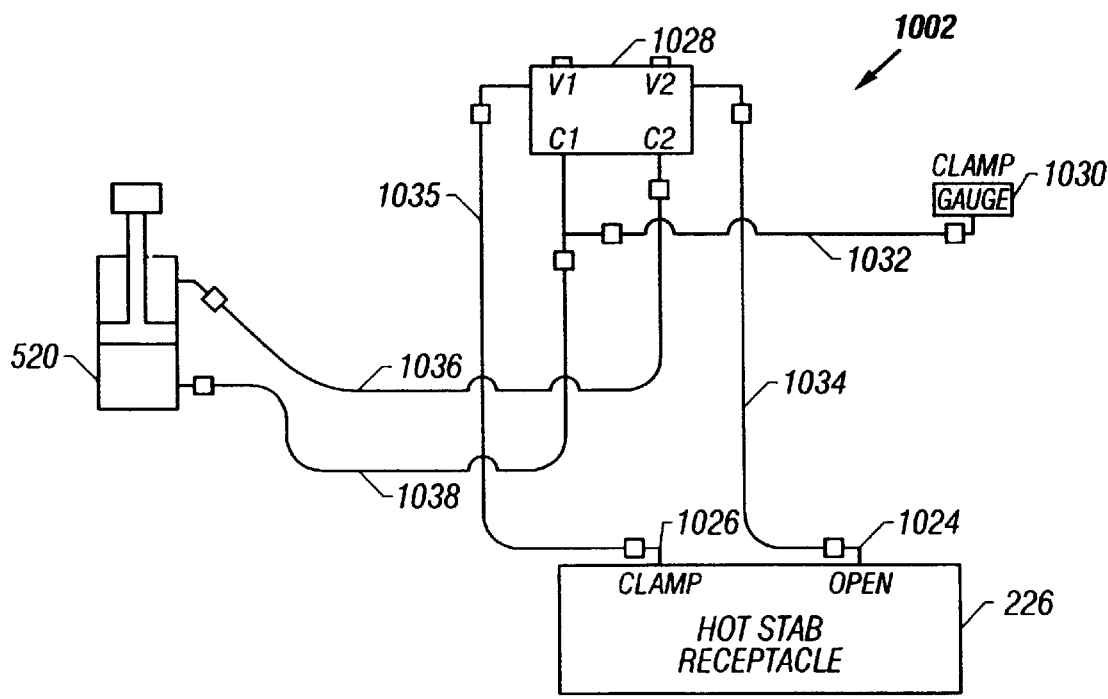
FIG. 16 is a schematic of the hydraulic system for the lower clamp of the present invention.

The seawater-pump 222 has variable pressure settings that are actuated by the ROV 30. Control of the clamps 230 and 612 (FIG. 12) and rod thruster assemblies 202 is through auxiliary solenoid valves 906, 1008 and 1028 (FIGS. 14, 15 and 16, respectively). The ROV 30 utilizes primary hydraulics for the caisson 102. The main pump/suction line of the caisson 102 is equipped with a breakaway feature, which allows recovery of the upper assembly in the event of an emergency or failure in the caisson 102.

The ROV 30 is equipped with a mating interface plate (not shown) that is utilized for interfacing with the caisson-mounted stab receptacle 226. The stab that is mounted on the ROV 30 will then de-couple from the ROV 30 after mating and, through a suitable flexible hose, allow the ROV 30 to travel a minimum of 10 feet away from the caisson 102 while remaining hydraulically coupled to the thruster unit 202. This procedure allows the ROV 30 to move around the seabed unit 10 and observe gauges and the various devices on the seabed unit 10 while being able to manipulate the hydraulic controls.

The Preferred Embodiment

The system of the present invention is shown in FIG. 1. The system comprises a seabed unit 10 that facilitates the use of various measuring devices such as cone rod 50 and buoy 40 assemblies. In addition to the seabed unit 10, a remotely operated vehicle (ROV) 30 is used to operate the seabed unit. Various measurement devices, such as cone rods 50, can first be inserted into the seabed unit 10 and, under the control of the ROV 30, can then be inserted into the seafloor 60 to a prescribed depth from which measurements and samples can be taken. All of these functions can be controlled remotely from the support ship 20.

As shown in FIG. 2, the seabed unit 10 is constructed in two major sections: the caisson 102 and the thruster unit 202. When in operating position, the caisson 102 is partially implanted into the seafloor 60 itself with the thruster unit 202 atop the caisson 102. Controls and measuring devices are positioned along the periphery of the thruster unit 202 to enable the ROV 30 to manipulate the controls and to observe the measuring devices. The seabed unit 10 is equipped with four breakaway pins 128 (shown in FIGS. 3 and 17). The breakaway pins 128 can be pulled by the ROV 30 in order to separate the thruster unit 202 from the caisson 102 in case of emergency. The caisson 102 is preferably a circular caisson for ease of fabrication and soil sealing. However, the jacking unit 202 is preferably of square configuration for ease of deck handling. Moreover, the jacking unit 202 is bolted together from sections in order to facilitate air transportation of the unit.

The caisson 102 is used both as a platform for the thruster unit and for embedment into the seafloor 60 as shown in FIG. 1. Once embedded, the caisson provides a "reaction" against the forces created by the thruster unit as it inserts the measuring device into the seafloor 60. Most caissons derive their reaction from the friction forces generated along the side walls of the caisson 102.

The actual embedment of the caisson 102 can be accomplished by suction, deadweight, force, or vibration. Force embedment requires some device to simply push the caisson 102 into the seafloor. Deadweight embedment relies upon heavy weights attached to the caisson 102 that increase the weight of the seabed unit 10 and cause it to simply sink more deeply into the soil of the seafloor. In the case of vibration embedment, a vibrating device is attached to the caisson and activated, causing the caisson to literally shake itself into the seafloor. The suction method requires a pump to pump water out from the hollow cavity within the caisson itself. In the preferred embodiment of the present invention, the water from within the caisson 102 is sucked out by the seawater pump 222 that is operated by the ROV 30. Continuous suction can provide an additional reaction component. Consequently, a suction caisson 102 is a component of the preferred embodiment of the present invention. It will be understood, however, by those skilled in the art that alternative methods of caisson embedment are possible.

As shown in FIG. 2, the caisson 102 is fitted with a suction/injection pump 222. As mentioned previously, the seawater suction/injection pump 222 may be located on the caisson 102, on the thruster unit 202 adjacent to the caisson 102, or on the ROV 30. The seawater suction/injection pump 222, powered by the ROV 30, is used to remove seawater from the caisson 102 in order to develop a downward force called a "reaction." This reaction is used to further embed the caisson 102 into the soil of the seafloor 60 beyond that provided by the deadweight of the seabed unit 10. The amount of reaction available depends upon the depth of the water and the diameter of the caisson 102. Once embedded, sidewall friction is adequate to provide sufficient reaction to counteract the upward force that is encountered as the cone rod 50 is inserted into the seafloor 60 by the thruster unit 202. However, if additional reaction is needed, the seawater pump 222 may be activated continuously to provide still more reaction. Once testing is completed, the ROV 30 reverses the suction/injection pump 222, thereby pumping seawater into the caisson 102, overcoming the sidewall friction and forcing the latter from the seafloor 60. The seabed unit 10 can then be moved to another location for additional testing.

The ROV 30 controls the insertion of the cone rod measuring unit 50 into the cone receptacle 234 of the thruster unit 202. The cone rod 50 is fitted with a counterweight guide sleeve 212 assembly. As may be seen in FIG. 7, the guide sleeve 702 assembly is fitted into the thruster unit 202 by inserting the guide sleeve 702 into the cone receptacle 234 and then into the sleeve receptacle 228 (FIGS. 2 and 3). The guide sleeve 702 is used to protect the cone rod penetrometer 52 from damage during the mating process. Once in place, the guide sleeve 702 is locked into position.

A "hot stab" 226 is fitted onto the thruster unit 202 as shown in FIG. 2. A hot stab is a device that allows the hydraulic coupling of two separate hydraulic systems in deepwater. In this case, the hot stab 226 enables the ROV 30 to supply pressurized hydraulic fluid to, and to manipulate the actuation of, the various hydraulic actuators on the thruster unit 202 such as jack actuator 232. Using the hot stab 226, the ROV 30 can manipulate sequentially, the upper clamp 230 and the lower clamp on the lower jaw assembly 220 on the thruster unit 202 so that the cone rod 50 can be inserted or removed from the seafloor 60.

The Apparatus:

The Seabed Unit:

The seabed unit comprises two sections: the caisson and the thruster unit. Embodiments of the caisson 102 are shown in FIGS. 2 and 3. As shown in FIG. 3, the caisson 102 has an outer casing 104 with a top edge 114 and a bottom edge 116. In the preferred embodiment of the present invention, the caisson 102 has a diameter of eight feet and a height of eight feet.

A suction orifice 120 is fitted along the top edge 114 of the caisson 102. The suction orifice 120 is constructed and arranged so that the suction/injection pump 222 (see FIG. 2) can be fitted to the suction orifice 120 and allow seawater to be pumped from the interior 112 of the caisson 102. In order to support the load placed on the floor 124 (which forms the top cap of the caisson 102) along the top edge 114 of the caisson 102, a plurality of support members 122 are fitted underneath the floor 124 as shown in FIG. 3. The support members 122 internally brace the caisson 102 to limit penetration of the caisson 102 into the seafloor 60 and to limit bowing of the floor 124.

Within the hollow interior 112 of the caisson 102 is a guide cylinder 106 along the centerline 118 having an insertion end 108 at the top edge 114 of the caisson 102 and an expulsion end 110 at the bottom edge 116. The purpose of the guide cylinder 106 is to support the cone rod 50 from buckling. The diameter of the guide cylinder 106 is a function of the measuring device that will be used with the present invention. In the preferred embodiment of the present invention, the guide cylinder 106 has an inner diameter of two to three inches. The inner diameter of the guide cylinder 106 is larger than the outside diameter of the cone rod 50 that is used, along with an additional tolerance to allow the cone rod 50 to slide easily within the guide cylinder 106. In short, the diameter of the guide cylinder 106 may be increased or decreased to accommodate the specifications of the measuring device 50 that will be used.

The caisson 102 may be made of standard materials used for sub-sea applications. The caisson 102 is designed to achieve the required embedment into the seafloor 60 and to develop the reaction necessary to counteract the force generated by thrusting objects into the seafloor 60. The thickness and type of material must, of course, be sufficient to handle the corrosive deterioration encountered from interaction with the natural elements and the stresses imposed by the accompanying equipment of the present invention.

A thruster unit 202 sits atop the caisson 102 as shown in FIG. 3. In the preferred embodiment of the present invention, the thruster unit 202 has four legs 204. The legs 204 are constructed and arranged to form a truncated polyhedron. However, the present invention could work with as few as two legs and, of course, more than four legs so long as the structural loads are handled and sufficient space remains for the ROV 30 to manipulate control devices. Multiple legs 204 can be used, stacked one on top of the other, to build a taller thruster unit without requiring longer legs. For instance, an alternative embodiment of the thruster unit 202 is shown in FIG. 2. In that alternative embodiment, a first set of legs 204 for the truncated polyhedron extend only part of the height of the thruster unit 202, with the remainder of the legs 204 oriented vertically. It will be understood by those skilled in the art that legs 204 of the present invention can be arranged in a wide variety of patterns so long as the structural loads are handled without undue strain on the thruster unit 202.

As shown in FIG. 3, approximately midway up the polyhedron are cross members 206. The cross members 206 act as a brace to strengthen the legs 204 and to provide a platform for attaching first gauge panel 208 and the second gauge panel 210 as shown in FIG. 3. The gauge panels 208 and 210 are positioned so that the ROV can observe the gauges as it manipulates the controls on the thruster unit 202.

The thruster unit 202 has the same centerline 118 as the caisson 102. Along the centerline 118 and within the polyhedron formed by the legs 204, an exterior counterweight guide sleeve 228 is positioned near the top of the polyhedron 214 as shown in FIG. 3. The purpose and description of the exterior counterweight guide sleeve 228 will be discussed below.

Four guide bars 218 are attached to the counterweight guide sleeve 212 as shown in FIG. 3. The opposite ends of the guide bars 218 are attached to the bottom of the polyhedron 216. A lower jaw assembly 220 is slideably attached to the four guide bars 218 as shown in FIG. 3. The lower jaw assembly 220 is able to move up and down along the guide bars 218 A more detailed description of the lower jaw assembly 220 is discussed below. Although the preferred embodiment of the present invention utilizes four guide bars, alternative embodiments can use as few as one and, of course, more than four guide bars.

Figure 11:
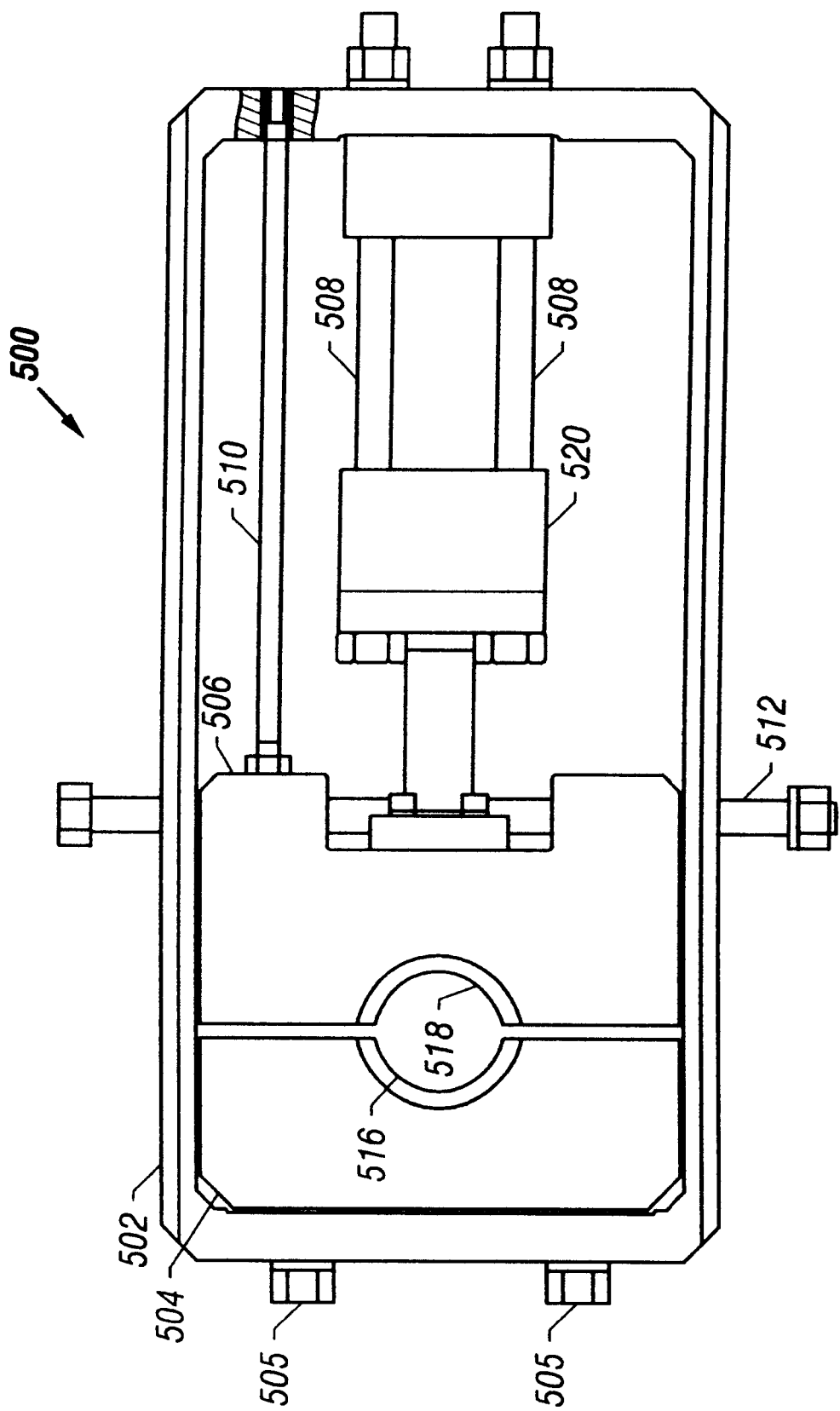
FIG. 11 is a top view of a rod section clamp of the thruster unit of the present invention.

FIG. 11 shows a top view of a clamp assembly 500. The clamp assembly 500 is used as the upper clamp 230 and as lower clamp 612 of the lower jaw assembly 220 of the thruster unit 202 (FIG. 3). As shown in FIG. 11, the clamp assembly 500 is comprised of a clamp housing 502. Within the clamp housing 502 is placed a static pad 504 having a first pad eye 516 against which the rod sections 56 are gripped. The static pad 504 is kept in place by retaining bolts 505. The movable pad 506 is placed opposite the static pad 504. As with the static pad 504, the movable pad has a second pad eye 518. The pad eyes 516 and 518 are constructed and arranged to clamp a rod section 56 of the cone rod 50 when the moveable pad 506 is moved toward the static pad 504 and to release the rod section 56 when the pads 504 and 506 are moved apart. Movable pad 506 is kept in proper orientation by guide bars 510 and 508 as shown in FIG. 11. In the preferred embodiment of the present invention, the moveable pad 506 is moved by one or more actuator rods 508 that are connected to one or more hydraulic actuators (not shown). While hydraulic actuation is preferred, it will be understood by those skilled in the art that other types of actuation may be substituted, such as electromagnetic actuators, electric motors, and the like.

Figure 12:
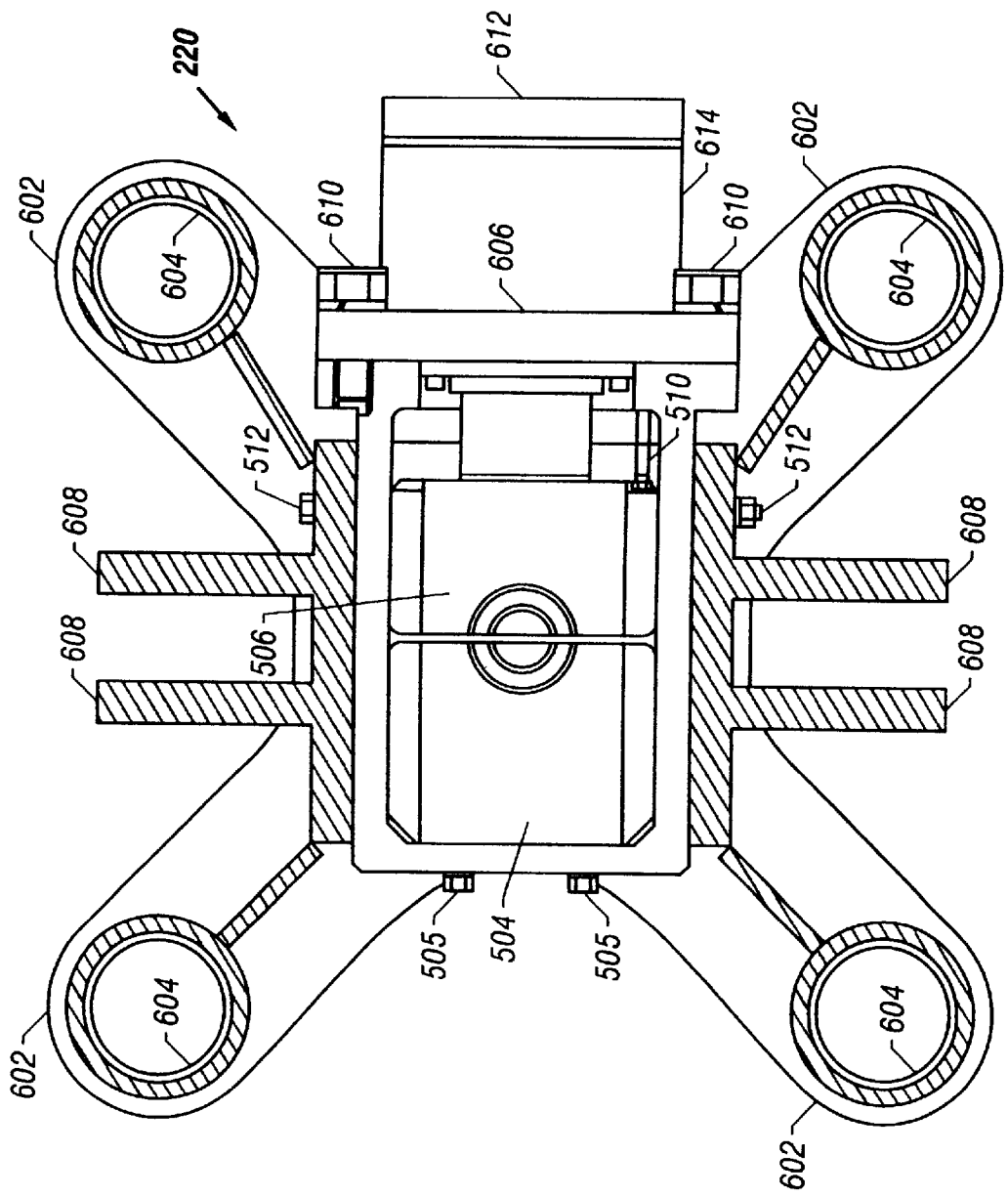
FIG. 12 is a top view of the lower jaw assembly of the thruster unit of the present invention.

FIG. 12 shows a top view of the lower jaw assembly 220. As shown in FIG. 12, the lower clamp 612 is centered within the lower jaw assembly 220 by attaching it to the mounting plate 606 via mounting bolts 610. An actuator housing 614 contains the hydraulic actuator that is used to move the moveable pad 506 toward or away from the static pad 504. As shown in FIG. 12, the lower jaw assembly 220 has four arms 602 spaced equally apart to form an X shape. Each arm 602 is equipped with a guide channel 604 though which the guide bars 218 (see FIG. 3) are inserted. This arrangement allows the lower jaw assembly to move slidably up and down along the guide bars 218. It will be understood by those skilled in the art that, although the preferred embodiment has four guide bars 218, as few as two guide bars, and of course more guide bars 218 may be employed. Finally, the lower jaw assembly is equipped with two sets of actuator mounts 608. The actuator mounts 608 are used to connect the jack actuator 232 (see FIGS. 2 and 3) to the lower jaw assembly.

All of the above elements of the seabed unit 10 are constructed and arranged to enable the ROV 30 to insert a penetrating cone and rod into the thruster unit 202 at the top of the polyhedron 214 through the counterweight guide sleeve 228 and through the caisson 202 along the centerline 118. The penetrating cone rod is then jacked, by successive up-and-down motions of the lower jaw assembly 220, into the seafloor 60 to the desired depth.

The Remotely Operated Vehicle (ROV)

In the preferred embodiment of the present invention, the ROV is a Triton XL that is rated for 8,000 feet depth. The Triton XL is available from STOLT COMEX SEAWAY INC. of 900 Town & Country Lane, Houston, Tex. 77024.

The Triton XL ROV is a free flying vehicle in that it maneuvers with its own thrusters and is able to move anywhere about the seabed unit 10. While the Triton XL satisfies the ROV 30 requirements for the present invention, it will be understood by those skilled in the art that alternative ROVs may be used, so long as they can affect hydraulic actuators on the seabed unit 10 and can monitor the effects of such actuation.

The ROV must be pre-configuration for various tooling and equipment. Preferably, these requirements should be accomplished prior to mobilization in order to minimize downtime and/or support vessel-related costs.

The support ROV system should support a minimum of 9 spare hydraulic circuits. These circuits are required for the functions shown in Table 1.

TABLE 1

ROV Hydraulic Functions

| FUNCTION | PRESSURE | FLOW RATE | VALVE TYPE |
| --- | --- | --- | --- |
| TORQUE tool rotate | 0-3000 psi | 2 GPM | bi-directional, 3pos, 4way, Open Center |
| TORQUE pawl latch | 0-3000 psi | 2 GPM | bi-directional, 3pos, 4way, Open Center |
| TORQUE pawl rotate | 0-3000 psi | 2 GPM | bi-directional, 3pos, 4way, Open Center |
| TORQUE tool tilt | 0-3000 psi | 2 GPM | bi-directional, 3pos, 4way, Closed Center |
| PENETRATION cylinder | 0-3000 psi | 5 GPM | bi-directional, 3pos, 4way, Open Center |
| UPPER release clamp | 0-3000 psi | 2 GPM | bi-directional, 3pos, 4way, Open Center |
| LOWER release clamp | 0-3000 psi | 2 GPM | bi-directional, 3pos, 4way, Open Center |
| ZIP pump reversal | 0-1700 psi | 2 GPM | bi-directional, 3pos, 4way, Open Center |
| ZIP pump | 0-3000 psi | 15 GPM | bi-directional, 3pos, 4way, Open Center |

The ROV hydraulic functions may be direct acting or operated through pilot operated external manifolds. All hydraulic functions are accomplished with pilot operated checks located in the manifold assembly (not shown) except for the Pawl Latch. Note that an external electrical interface to the ROV electrical system is required if a flowmeter is used.

Auxiliary tooling is required on the host ROV in order to accomplish various tasks during the measuring device installation sequence. These auxiliary tools consist of the following: a zip pump, an ROV stab, and a Grinder.

The present invention provides for acoustic tracking of the host ROV, a transponder on the thrusting unit, a transponder on the measuring device, and a transponder on the recovery wire. Coordination of frequencies will be required with the survey service provider and local rig/vessel operators.

The host ROV system should provide two multi-function manipulator systems, located on the port and starboard sides of the host ROV front porch assembly. The manipulator systems should satisfy the performance as described in Tables 2 and 3. While these are suggested requirements, it will be understood by those skilled in the art that modification of stab interfaces, gauges, and other equipment can alter these requirements.

TABLE 2

Starboard Manipulator Requirements

| Manipulator | Function | Range |
| --- | --- | --- |
| Starboard | Shoulder Azimuth | 275° |
| Starboard | Shoulder Elevation | 120° |
| Starboard | Elbow Pivot | 120° |

TABLE 2-continued

Starboard Manipulator Requirements

| Manipulator | Function | Range |
| --- | --- | --- |
| Starboard | Wrist Pitch | 200° |
| Starboard | Wrist Yaw | 200° |
| Starboard | Wrist Rotate | 360°continuous |
| Starboard | Reach | 64" |
| Starboard | Maximum Lift | 200 Lbs. |
| Starboard | Jaw Force | 300 Lbs. |
| Starboard | Wrist Torque | 100 ft. lbs. |

TABLE 3

Port Manipulator Requirements

| Manipulator | Function | Range |
| --- | --- | --- |
| Port | Shoulder Azimuth | 275° |
| Port | Shoulder Elevation | 90° |
| Port | Elbow Pivot | 100° |
| Port | Wrist Pitch | 100° |
| Port | Wrist Yaw | 120° |
| Port | Wrist Rotate | 360°continuous |
| Port | Reach | 60" |
| Port | Maximum Lift | 770 Lbs. |
| Port | Jaw Force | 450 Lbs. |
| Port | Wrist Torque | 80 ft. lbs. |

The Measuring Devices

Figures 4, 5:
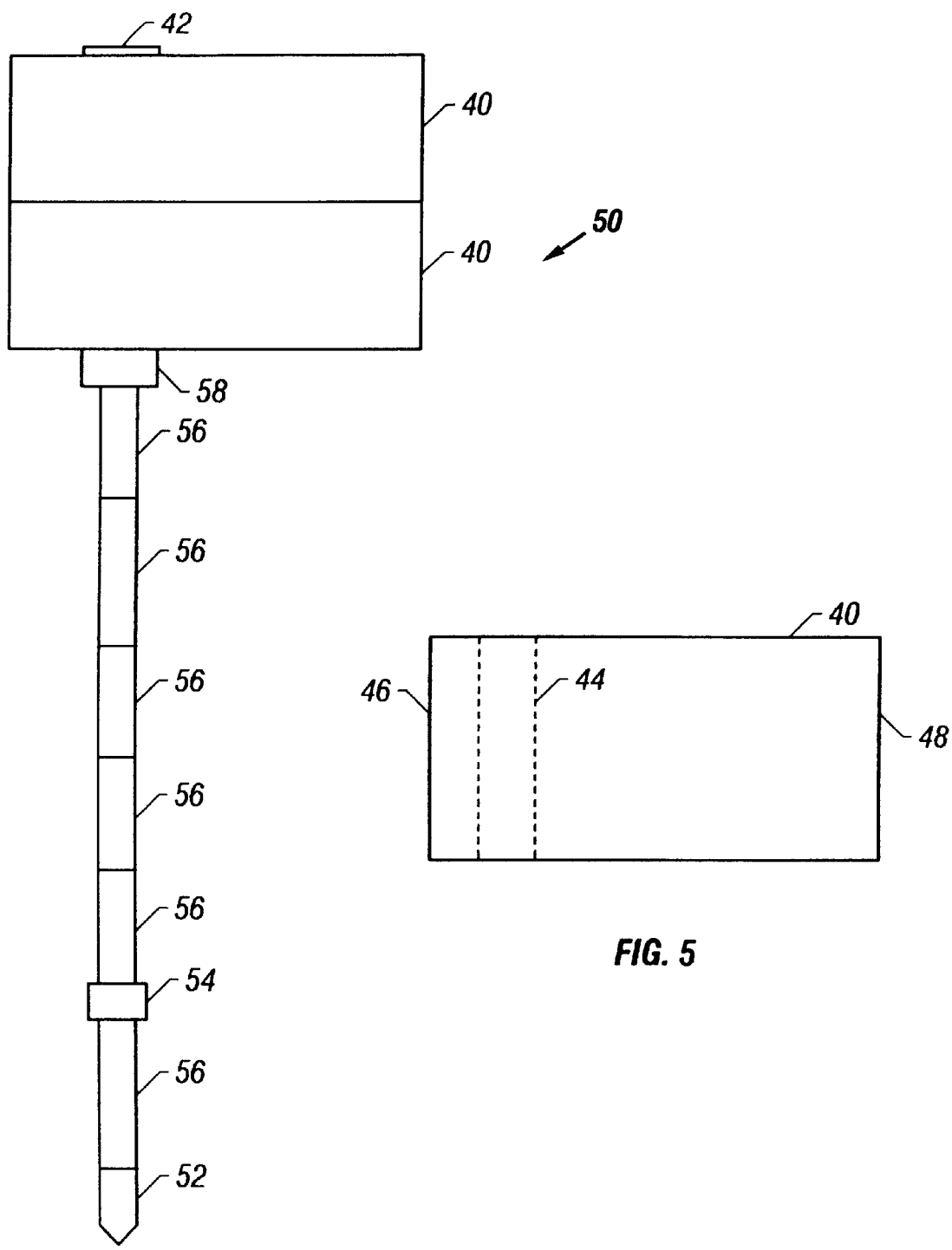
FIG. 4 is a side view of a cone rod assembly of the present invention.
FIG. 5 is a side view of a buoy for the cone rod assembly of the present invention.

In the preferred embodiment of the present invention, the intended measuring device is a cone rod 50 as shown in FIG. 2. It will be understood by those skilled in the art that a wide variety of other measuring devices can be utilized with the present invention and that the following description is merely illustrative of one such measuring device. Referring now to FIG. 4, a cone rod 50 is comprised of a memory cone penetrometer 52 and a plurality of rod sections 56. The rod sections 56 may all be the same length, or they may be of variable lengths. One or more rod sections 56 are fastened together, and then fastened to the memory cone penetrometer 52, to achieve the desired length, forming a cone rod 50. In the preferred embodiment of the present invention, the rod sections 56 are threadably fastened together in order to present a smooth, continuous outer surface. However, those skilled in the art will recognize other fastening means to join the rod sections 56 and the cone penetrometer 52 that satisfy the topology requirements of the surface of the cone rod 50.

Figure 6:
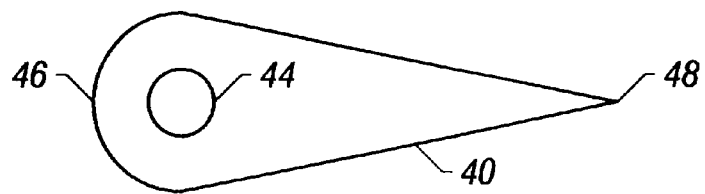
FIG. 6 is a top view of a buoy for the cone rod assembly of the present invention.

At the top end of the cone rod 50 are one or more buoys 40. The buoys 40 are shown in more detail in FIGS. 5 and 6. As shown in FIG. 6, the buoy 40 has a leading edge 46 and a trailing edge 48. The buoy 40 has a hydrodynamic shape as shown in FIG. 6 in order to reduce drag. Such drag could be caused by, for example, undersea currents acting upon the buoy 50 and the cone rod 50 while being kept in a stationary position. Consequently, the hydrodynamic shape of the buoy 40 will vary in order to minimize drag which, of course, depends upon the expected velocity of the undersea currents to be encountered. Finally, the buoy 40 has a chamber 44 as shown in FIG. 6. The chamber 44 is constructed and arranged to accommodate cylindrical packages and/or rod sections 56 and/or any other cylindrical objects attached to the cone rod 50. The purpose of the buoy is to keep the cone rod 50 in a vertical orientation while it is lowered to the seafloor 60 and to keep the cone rod 50 in tension when the lower portion of the rod is clamped or weighted down. Thus the amount of tension on the cone rod 50 can be adjusted by varying the number and size of the buoys 40. Finally, the buoy 40 may be fitted with football floats or beacons (not shown) to facilitate handling by the ROV 30 or by crewmen aboard the support ship 20.

Referring again to FIG. 4, a friction reducer 54 is attached to the cone rod 50 in proximity to the memory cone penetrometer 52. A universal cone rod stop 58 is attached near the end opposite the memory cone penetrometer 52, adjacent to the lowermost buoy 40 as shown in FIG. 4. The universal cone rod stop 58 is used to prevent over-extension of the cone rod 50 into the seafloor 60 that could possibly damage the buoys 40. The buoys 40 are thus bracketed by the universal cone rod stop 58 and the end cap 42 as shown in FIG. 4. As the electronics package is contained within the buoy 40 (specifically the chamber 44), the electronics package 59 is thus positioned adjacent to the universal cone rod stop 58.

Figure 10:
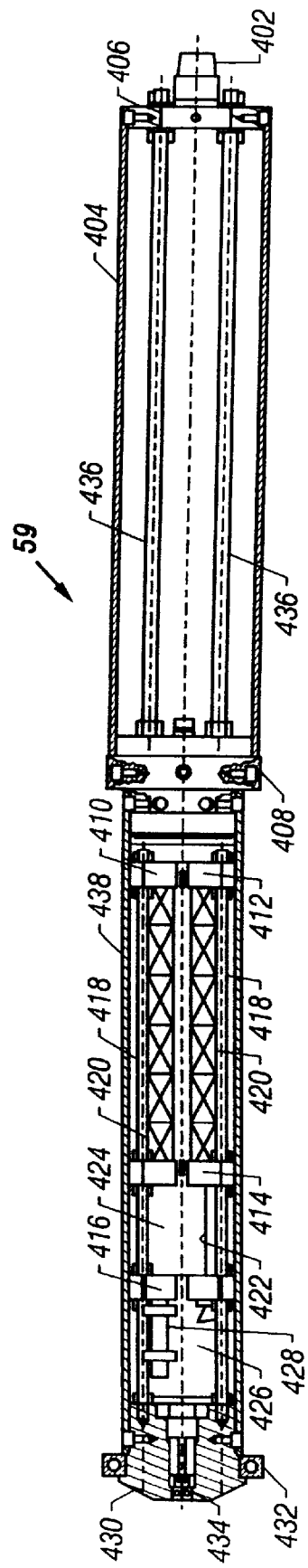
FIG. 10 is a cross-sectional view of an electronic package that is a component of the present invention.

FIG. 10 shows a cross-sectional view of electronic package 59. As shown in FIG. 10, a vertec thread 402 is used to connect the electronic package to the uppermost rod section 56 of the cone rod 50. A cover sleeve 404 is capped by a lower housing 406 and a bushing 408 as shown in FIG. 10. Within the cover sleeve 404 are one or more spacer rods. The spacer rods 436 and the length of the cover sleeve 404 are used to provide adequate spacing between the cone rod 50 and the electronics section housed within the spacer tube 438. The spacer tube 438 is constructed and arranged to fit within the chamber 44 of the buoy 40. Multiple spacer tubes 438 could be staked in sequence and stored within the channels 44 of multiple buoys 40 if necessary.

Within the spacer tube 438 is a middle body 410 adjacent to the bushing 408. Adjacent to the middle body 410 on the side opposite the bushing 408 is the lower body mount 412. Farther down the spacer tube 438 from the lower body mount 412 lies upper body mount 414. The upper body mount 414 is connected to the lower body mount 412 via round bars 418. Within the round bars 418 are batteries 420 as shown in FIG. 10. Between upper body mount 414 and upper body mount 414 is the plug mounting 416 which forms a first circuit bay 424 and a second circuit bay 426. One or more circuit boards 422 can be housed within the first circuit bay 424. The circuit boards 422 can contain microprocessors or related chips as well. Moreover, the circuit boards 422 can contain various types of memory, such as RAM, ECC RAM, flash memory, EEPROMs, and the like. A modem 428 can be housed in the second circuit bay 426 as shown in FIG. 10. The curcuit boards 422, the batteries 420 and the modem 428 are used to acquire, process, store and/or transmit data taken from the memory cone penetrometer 52. The bearing 432 is connected to one end of the buoy 40. The bearing 432 allows the electronic package to swivel within the chamber 44 of the buoy 40 or, in other words, to allow the buoy 40 to swivel in the ocean currents without imparting a torque on the electronic package 59 and, subsequently, on the cone rod 50. Finally, an electronic connector 434 is provided to connect, electrically, the circuitry stored within the spacer tube 438 to the support ship 20 or to the ROV 30. The electronics package itself is typically "hidden" within the chamber 44 of the buoy 40 in order to minimize the drag imparted by ocean currents.

Figure 7:
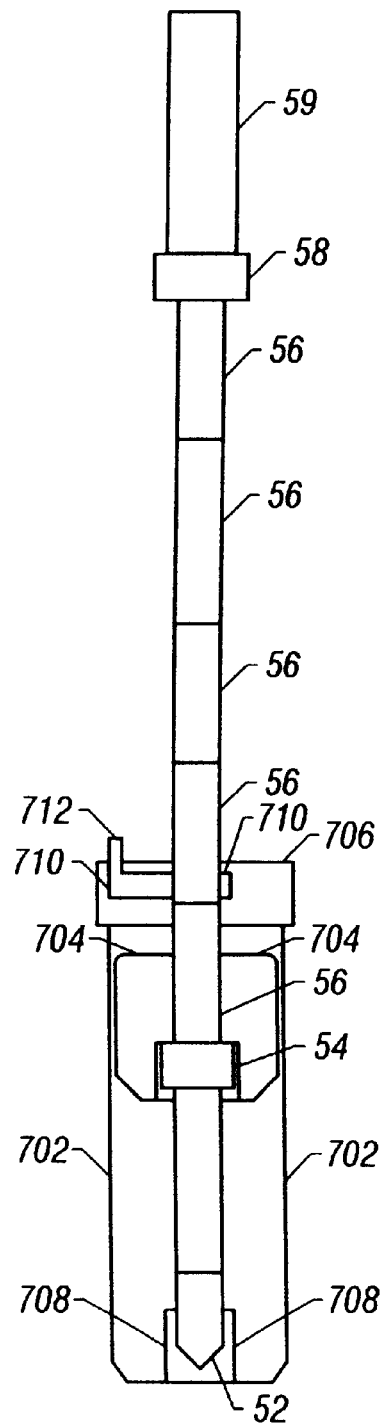
FIG. 7 is a side view of a cone rod assembly showing a sectional view of the guide sleeve of the present invention.

Another side view of the cone rod 50 is shown in FIG. 7. In this view, the electronic package 59 is shown attached to the top of the universal cone rod stop 58. The electronic package 59 contains the electronics for storing information obtained from the memory cone penetrometer 52. For example, the electronic package 59 could contain an acoustic beacon to help the ROV locate the seabed unit 10. In another embodiment, the electronic package 59 contains telemetry equipment that can, upon signals from the support ship 20 or the ROV 30, manipulate electronic or hydraulic controls on the seabed unit 10. The electronic package 59 is constructed and arranged to fit within the chamber 44 of the buoy 40. As multiple buoys 40 may be attached to the cone rod 50, so may multiple electronic packages 59 by stacked, one or more, each within the multiple buoys 40.

Referring again to FIG. 7, a guide sleeve 702 is fitted onto the end of the cone rod 50 in proximity to the memory cone penetrometer 52. The guide sleeve 702 is used to mate the cone rod 50 (which is lowered separately from the support ship 20) into the seabed unit 10. Moreover, the guide sleeve 702 protects the delicate memory cone penetrometer 52 from damage during the mating process.

The guide sleeve 702 is fitted with a latch frame 706 as shown in FIG. 7. The latch frame 706 serves to lock the guide sleeve 702 into the thruster unit 202 of the seabed unit 10 when the guide sleeve 702 is properly positioned within the thruster unit 202. Contained within the guide sleeve 702 is a counterweight 704. The counterweight 704 is constructed and arranged to slide vertically within the interior of the guide sleeve 702. The counterweight 704 is used to stage the cone rod in the jacking clamps 203 and 612.

As shown in FIG. 7, the counterweight 704 is placed around the rod section 56 above the (larger diameter) friction reducer 54 so that, when the cone rod assembly 50 is oriented vertically, the counterweight 704 acts upon the friction reducer 54 and forces the cone rod 50 downward. To prevent premature release of the counterweight 704 from its pre-insertion position at the top of the guide sleeve 702 (as shown in FIG. 7), a rod latch 710 is positioned within the latch frame 706 to lock the cone rod 50 and the latch frame 706 together. A latch release 712 of the rod latch 710 is positioned at the top of the latch frame 706 as shown in FIG. 7. An alternate embodiment of the latching mechanism could lock the counterweight 704 instead of the cone rod 50. In any case, at the proper time during the insertion operation, the latch release 712 is thrown by the ROV 30, thereby releasing the cone rod 50 and allowing the counterweight 704 to insert the cone rod 50 into the lower jaw assembly 220 of the thruster unit 202. The latch release 712 is automatically re-latched upon recovery of the cone rod 50.

As a final precaution, a guide channel 708 can be provided at the end of the guide sleeve 702 in proximity to the memory cone penetrometer 52 as shown in FIG. 7. The guide channel 708 must be larger in diameter than the universal cone rod stop 58 so that the cone rod 50 may be jacked into the seafloor 60.

FIGS. 8 and 9 show the guide sleeve 702 in more detail. As shown in FIG. 8, the guide sleeve 702 is comprised of a cylindrical hollow sleeve 716 having three or more guide flanges 714 that help center the guide sleeve 702 along the same centerline as the thruster unit 202. The sleeve 716 has a proximal end 720 and a distal end 722 as shown in FIG. 8. The distal end 722 of the sleeve 716 is fitted with a collar 724 to which the latch frame 706 is attached. A rod section 56 of the cone rod 50 is shown protruding from the distal end of the guide sleeve 702.

Within the latch frame 706 is a rod latch 710 (shown in FIGS. 7 and 9). The rod latch 710 has a latch release 712 comprised of a left latch handle 726 and a right latch handle 728 which, when squeezed together by the ROV 30, releases the rod latch 710 and allows the cone rod 50 to move vertically within the guide sleeve 702. A safety stop 718 is placed over the latch frame 706 to prevent the downwardly moving buoy from damaging the latch handles 726 and 728 and vise-versa. The inner diameter of the safety stop 718 is greater than the outer diameter of the cone rod 50 so that the safety stop 718 does not impede the vertical motion of the cone rod 50.

FIG. 9 shows a cross-sectional side view of the guide sleeve 702. As shown in FIG. 9, the sleeve 716 is hollow. As described before, the cone rod 50 is fitted with a friction reducer 54 that is of slightly larger outside diameter that the rod sections 56. This enables the counterweight 704 to be fitted around one of the rod sections 56 and abut the friction reducer 54 so that, when the rod latch 710 is released, the counterweight 704, acting upon the friction reducer 54, forces the cone rod 50 downward. This also allows the friction reducer 54 to lift up the counterweight 704 for resetting the sleeve assembly during recovery. Finally, a pad eye 730 is fitted onto the latch frame 706 to facilitate assembly and handling.

The guide sleeve is typically assembled on location at the surface of the testing site aboard the support ship 20. First, one or more rod sections 56 are attached to a memory cone penetrometer 52. At a predetermined length, the friction reducer is then attached to the top end of the topmost rod section 56. Thereafter, at least one additional rod section 56 is then attached to the friction reducer 54 to form the new topmost rod section 56. The new topmost rod section 56 is then inserted into the centerline hole 732 of the counterweight 704 and the counterweight 704 is slideably moved toward the memory cone penetrometer 52 until it is stopped by the friction reducer 54 by virtue of the friction reducer's outside diameter being larger than the diameter of the centerline hole 732. The cone rod 50, with the counterweight 704 is then placed within the interior of the sleeve 716 as shown in FIG. 9. The latch frame 706 is then placed over the topmost rod section 56 and then bolted to the collar 722 of the sleeve 716. Once in position, the rod latch 710 is then engaged, thereby locking the cone rod 50 into place with respect to the guide sleeve 702. The safety stop 718 is then placed over the topmost rod section 56 and slid into position as shown in FIG. 9. After the guide sleeve 702 has been attached to the cone rod 50, the remaining rod sections 56 are attached until the cone rod 50 reaches its desired length. Thereafter, the universal cone rod stop 58 is attached to the topmost rod section 56 and the electronic package 59 is attached to the universal cone rod stop 58 as shown in FIG. 7. Finally, one or more buoys 40 are then attached to the universal cone rod stop 58 and/or the electronic package 59 to achieve the desired amount of buoyancy/tension on the cone rod 50.

The Hydraulic System

The hydraulic system of the seabed unit 20 of the preferred embodiment comprises four actuators and one valve. There is one actuator each for the upper clamp 230 and the lower clamp 612 stored, for example, in the actuator housing 614 as shown in FIG. 12. The remaining two actuators are the jacking actuators 232 (see FIGS. 2 and 3).

The hydraulic system of the seabed unit 10 is shown in FIGS. 13–16. The clamp actuators 520, for the upper clamp 230 and the lower clamp 612, preferably are able to operate at twenty gallons per minute (20 gpm) at 1500 psi pressure. The jacking actuators, on the other hand, preferably are able to operate at five or fifty gallons per minute (5 gmp or 50 gmp) at 1500 psi pressure. Note, however, that the 1500 psi operating pressure is in addition to the 4000 psi or more hydrostatic water pressure at the depth of 5000 feet.

Figure 13:
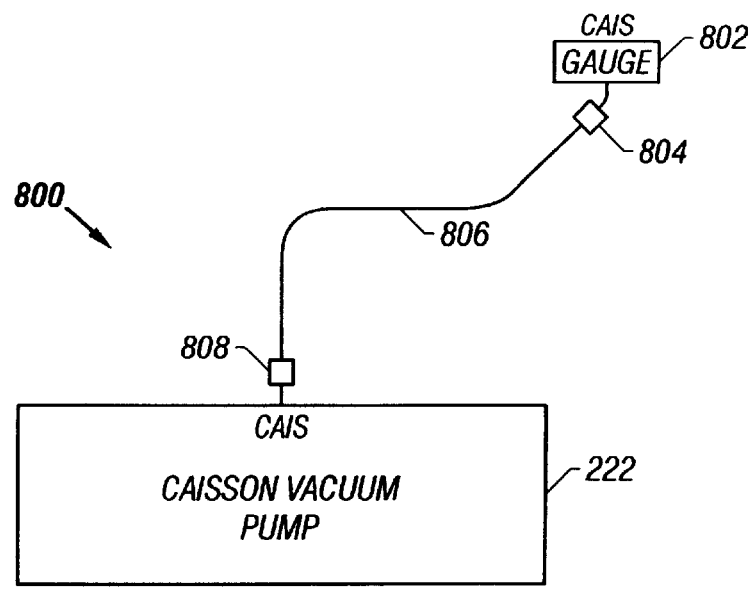
FIG. 13 is a schematic of the hydraulic system for the caisson of the present invention.

The hydraulic subsystem 800 for the caisson is shown in FIG. 13. The caisson hydraulic subsystem is comprised of the caisson vacuum pump 222 that is connected to a hose 806 via an interconnect 808. The hose 806 in turn is connected to the CAIS gauge 802 by the interconnect 804. The CAIS gauge 802 is situated on a second gauge panel 210 as shown in FIG. 3. By situating the gauge 802 on the gauge panel 210, it can be viewed by the ROV 30 from a convenient location while it is operating the pump 222.

The jacking actuator hydraulic subsystem 900 is shown in FIG. 14. The power for the hydraulic system is supplied by the ROV 30 via the hot stab receptacle 226. An acceptable hot stab receptacle 226 is the model MDC-10/9-ROV Operated Multi Connector that is manufactured by UnTech Company. In the jacking actuator hydraulic subsystem 900 has two main branches: push and pull for pushing the measuring device into the seafloor and pulling it out again, respectively. One of the several receptacles of the hot stab receptacle 226 is pull receptacle 920. As shown in FIG. 14, the pull receptacle 920 is connected to hose 912 that connects the hot stab 226 to the control valve 906. Similarly, the push receptacle 922 is connected to the control valve 906 by hose 918. The output of the control valve 906 is transmitted to two hoses 914 and 916 as shown in FIG. 14. Hoses 908 and 910 tap into hoses 914 and 916, respectively, to facilitate monitoring via pull gauge 902 and push gauge 904. The push gauge 904 and the pull gauge 902 are positioned on the first gauge panel 208 as shown in FIG. 3 for convenient monitoring during operation by the cameras fitted on the ROV 30. Pull hose 914 branches out to the pull inputs 926 on the jacking actuators 232. Similarly, the push hose 916 branches out to the push inputs 928 of the jacking actuators.

The hydraulic subsystems for the clamping actuators 520 are shown in FIGS. 15 and 16. Starting with the hold subsystem for the upper clamp 230 shown in FIG. 15, the hot stab receptacle 226 has an open receptacle 1004 that is connected to the control valve 1008 via hose 1014. Similarly, the hold receptacle 1006 of the hot stab 226 is connected to the control valve 1008 via hose 1015. The outputs of the control valve 1008 feed into hoses 1016 and 1018 that operate the clamp actuator 520 of the upper clamp 230. Hold gauge 1010 is connected to hose 1018 via hose 1012. The hold gauge 1010 is fitted onto the second gauge panel 210 (see FIG. 3) to provide convenient monitoring by the cameras of the ROV 30 during operation.

While on separate lines, the hydraulic subsystems for the two clamping actuators 520 are essentially identical. The clamp subsystem for the lower clamp 612 shown in FIG. 16, the hot stab receptacle 226 has an open receptacle 1024 that is connected to the control valve 1028 via hose 1034. Similarly, the hold receptacle 1026 of the hot stab 226 is connected to the control valve 1028 via hose 1035. The outputs of the control valve 1028 feed into hoses 1036 and 1038 that operate the clamp actuator 520 of the lower clamp 612. Clamp gauge 1030 is connected to hose 1038 via hose 1032. The hold gauge 1030 is fitted onto the first gauge panel 208 (see FIG. 3) to provide convenient monitoring by the cameras of the ROV 30 during operation.

It will be appreciated by those skilled in the art that the seabed unit 10 can accommodate many different types of measuring devices, and that the accompanying claims are not limited to the above-illustrative description of one type of measuring device.

The Support Ship

The present invention can be deployed from a Class II dynamically positioned ROV support vessel such as the Seaway Legend. The Seaway Legend is available from the STOLT COMEX SEAWAY INC. of Houston, Tex. However, any ship that can maintain a position over a particular point in the ocean, and carry and lower a ten to fifty ton load from a winch, can be used. Unlike the support ships in the prior art, large drillships with a drilling rig and pipe are unnecessary with the present invention.

Method of Operation

The following technical procedure describes the installation, testing (using the cone penetrometer rod 50), and the removal sequence of the seabed unit 10 using the ROV 30. These procedures are divided into five sections: launch, sub-sea installation, penetration of the penetrometer rod into the seafloor and subsequent testing therewith, rod retrieval, and system recovery aboard the support ship.

Launch

The relatively small size of the present invention enables side launching as well as stern launching (both vertically and horizontally). In addition, bow and stern slingshot launches are also possible with the present invention. The launch itself should occur in fair weather. The caisson 102 is positioned horizontal on the deck of the support ship 20. The thrusting unit 202 is then attached to the caisson 102 via breakaway pins 128. The breakaway pins 128 typically utilize a power thread actuation. Note, unlike prior art systems, the measuring device, in this case the cone rod 50, is not placed into the thruster unit 202 while on the surface. Instead, the cone rod 50 will be mated with the thrusting unit at the seafloor site 60, eliminating the need for cumbersome and entangling guidelines. This allows horizontal deployment of the jacking unit and enables use of a wider variety of support vessels than was available in prior art systems.

Next, two butterfly vent valves 126 on the top of the caisson 102 (see FIG. 17) are opened to release air in the caisson and facilitate the lowering of the caisson 102. Finally, a transponder (not shown) is attached to the top of one of the thrusting unit support legs 204 by a bracket to finish the preparation for launch of the seabed unit 10.

The winch deployment (upper drum) wire is run through a pelican hook on the caisson 102 and attached to the bale (not shown). The winch launch and recovery system ("LARS") wire (lower drum) is attached to the bale. Both sides of the caisson assembly have 4×6 wooden bumpers and the decking has wooden rails to help the assembly slide. The support vessel's A-Frame (not shown) is placed in launch and deployment position. On the support ship 20, the upper drum deployment wire and lower drum LARS wire are initially heaved in and put under tension. The seabed unit 10 is then skidded approximately 3 to 5 ft. over the stern by simultaneously heaving in on the deployment wire and paying out on the LARS. Next, the deployment line is released from the Pelican hook utilizing a soft line. Note that overboarding loads are carried primarily by the LARS wire until the caisson 102 is completely overboard.

Once the seabed unit 10 has been launched, the A-Frame gantry of the support vessel 20 is moved in-board of the stern of the vessel as required to keep the caisson 102 against the stern of the vessel 20. Once the seabed unit 10 is overboard, the operators then slack and remove the LARS wire. Next, the support vessel's 20 A-Frame gantry is moved into deployment position. The seabed unit 10 is then lowered to a depth of approximately 300 feet where the lowering will be stopped and held until the ROV 30 is deployed and lowered to inspect the seabed unit 10. The ROV 30 is deployed by lifting it off the deck with the ship's handling system and then lowering it into the water.

The ROV 30 checks to see if the seabed unit 10 is in a substantially vertical orientation and to ensure that nothing has become entangled, and that the seabed unit 10 is otherwise ready to be lowered to the seafloor 60. Once ready, the seabed unit 10 is lowered to the seafloor 60 at rate of approximately 100 to 300 feet per minute (fpm), however that rate is slowed to approximately 20 to 25 fpm when the caisson 102 has been lowered to about 300 feet from the seafloor 60. When the seabed unit 10 approaches approximately 100 feet from the bottom, it will be stopped so that the ROV 30 can once again inspect it. Although these inspection stops may be skipped, they are helpful to ensure that no preventable problems are encountered during the subsequent embedment phase.

Embedment

The seabed unit 10 is lowered to the bottom until it stops penetrating the soil under its own dead weight. The suction caisson 102 is expected to embed to about one-half of its final embedment depth by its submerged weight alone. The ROV 30 observes the embedment marks on the suction caisson 102 and the optional level bubble (not shown) on the caisson 102.

If the suction caisson 102 is within five (5) degrees of a vertical orientation (as measured by a line perpendicular to the seafloor 60 and the centerline 118 of the suction caisson 102, then the remaining actions are to be carried out. However, if the vertical orientation of the seabed unit 10 is outside of the five degree limit, then the seabed unit 10 will be raised and relocated to another position and then lowered into the seafloor 60 again.

Once lowered, the load line hook is disconnected from the thruster unit 202 bale (not shown). The ROV 30 closes the two vent valves 126. Typically, the closing of the vents will require a ¼ turn of the butterfly valves 126. Each butterfly valve 126 requires about 65 ft-lb. to open at a differential pressure of 16 bar. The arm of the preferred embodiment of the ROV 30 is rated for 100 ft-lb. which will be adequate to open and to close the butterfly valve 126.

Once the butterfly valves are closed, the ROV 30 operator will then hook up the hydraulic connections using the hot stab receptacle 226 on the seabed unit 10. The ROV 30 is then maneuvered to an observation position where its cameras can see the indicator panels 208 and 210 as well as the suction caisson 102 depth paint lines. At this point, the ROV 30 will be able to grab the thrusting unit 202 with its manipulator arm and use its altimeter to detect the change in depth.

The ROV 30 starts the suction caisson pump 222. The pump 222 will be stopped when the top 114 of the suction caisson 102 is about one foot above the seafloor 60. In so doing, the cameras of the ROV 30 will observe the depth marks until the suction caisson 102 reaches the seven (7) foot mark.

The pressures will be observed by the ROV 30 operator to ensure that no negative pressure differential is greater than 3 PSI. If the pressure goes up, the pumping is stopped and the situation is evaluated. In evaluating the situation, the pump 222 is started and the results observed. If the pressure goes up again, or does not reach the negative pressure differential of 8 PSI, a fault is declared and the procedure is aborted.

If the caisson 102 is of the diameter of the preferred embodiment (eight feet), the hydrostatic pressure differential along the top edge 114 of the caisson 102, and of course the friction generated by the soil on the caisson casing 104, will provide 15,000 to 40,000 pounds of vertically oriented force. This downward force is called a "reaction" and is a function of the water depth, the diameter and height of the caisson 102, and whether or not continuous suction is applied. It should be noted that reaction is necessary to counteract the upward force generated by forcing the cone rod 50 into the seafloor 60. If necessary, the dimensions of the caisson 102 can be increased to create additional reaction. This is helpful, for example, if the depth of penetration is deeper, or if larger diameter penetrometers are used. It will be understood by those skilled in the art that the caisson 102 is to be designed to achieve sufficient reaction to enable the thruster unit 202 to thrust the cone rod 50 into the seafloor 60 to the desired depth. Moreover, the caisson 102 is to be designed to withstand the hydrostatic pressures required to imbed the seabed unit 10 into the soil of the seafloor 60 and to withstand the overpressure needed to remove the caisson 102 from the seafloor 60 upon completion of testing. If necessary, the ROV 30 can activate pump 222 to provide continuous (active) suction on the caisson 102.

Mating and Jacking

A cone rod 50, 150-foot or more in length is deployed over the starboard side of the support vessel 20 and lowered by a ⅜ inch armored electrical cable by a 5,000 lb. drum winch from the support vessel 20. As the cone rod assembly 50 is being lowered to the seafloor 60, the depth below sea level will be monitored by a payout indicator via an instrumented 22-inch diameter sheave. As the cone rod 50 is an assembly separate from the thruster unit 202, the two must be mated. The ROV 30 thus grasps the cone rod 50 and guides it into the exterior guide sleeve receptacle 228 of the thrusting unit 202.

The vessel 20 slackens the wire on the cone penetrometer rod 50 when the thrusting unit 202 clamps the rod 50. As mentioned previously, the cone penetrometer rod 50 is supported from its top by a series of low drag coefficient buoys 40. Typically, three buoys 40 will meet the vertical buoyancy requirements of a 150-foot cone rod penetrometer assembly 50.

The ROV 30, through its operator, observes and controls the driving of the penetrometer rod into the ground. The lowering operation consists of repeated cycles having the six 6 steps shown in Table 4 until the desired testing depth is reached.

TABLE 4

Jacking Sequence

1. Close the lower clamp 612
2. Open the upper clamp 230
3. Extend the jacking actuator 232 while monitoring the pressure gauge 904 and flow meter (incorporated into the pressure gauge 904)
4. Close the upper clamp 230
5. Open the lower clamp 612
6. Retract the penetration cylinders 232

The cone rod 50 is pushed to the desired penetration in a series of 4 ft. strokes. Some data collection from the penetrometer 52 takes place during the jacking phase. This data collection is time-synchronized with the jacking actuation steps. The time synchronization is done electronically as part of the process (i.e., some information is shared between the ROV 30 which initiates the actuation and the cone rod's electronics package 59 which receives and stores the penetrometer data). In the preferred embodiment of the present invention, there is an onboard autonomous data storage within the electronics package 59 and a simultaneous real-time data transfer to the support ship 20 and to the ROV 30.

If a problem is encountered, such as hitting a underground rock, there will be an sharp or step increase in the pressure measured in gauge 904 and the flow meter will show zero which indicates that the rod 50 cannot be pushed any further. Special attention must also be paid to the possibility of buckling the rod 50 made evident by a sudden drop in pressure measured in gauge 904. If the rod 50 buckles, all penetration must stop immediately.

As the cone rod 50 is being pushed into the soil, the cone data will be recorded within the remote memory unit of the electronics package 59 and transmitted to the vessel via the electrical wireline mentioned previously. In the preferred embodiment of the present invention, four data channels are monitored. The four channels are: Point resistance, Sleeve Friction, Dynamic Pore Pressure, and Flow rate.

Recovery

After penetration has stopped, the memory cone penetrometer 52 will be backed out of the soil until it hits a mechanical stop and will not rise any more. The recovery utilizes the steps shown in Table 5 (which are, essentially, the steps of Table 4 in reverse order). In order to ensure that the cone rod 50 is not ejected from the thrusting unit 202, the lower clamp 612 will remain clamped around the cone rod 50 at all times except when the lower clamp 612 is being repositioned. Because of the construction and arrangement of the elements of the thrusting unit 202, the lower clamp 612 cannot extend to the top of the thrusting unit 202.

Again, the ROV 30 observes and controls the raising of the cone rod 50 out of the ground. The raising operation consists of repeated cycles of the six steps shown in Table 5 until the measuring device is recovered.

TABLE 5

Cone Rod Retraction Cycle

1. Close the lower clamp 612
2. Release the upper clamp 230
3. Retract the jacking actuators 232 while monitoring the pull gauge 902
4. Close the upper clamp 230
5. Open the lower clamp 612
6. Extend the jacking actuators 232 in order to reposition the lower clamp 612 for the next cycle If the pressure observed in gauge 902 goes up substantially when actuating the jacking actuators 232, the operator checks to ensure that the upper clamp 230 is open. If it is open, the operator then checks to make sure nothing is hung up on the rod.

Open both clamps 203 and 612 when ready to remove the cone rod 50. After the rod 50 stops rising from the jacking operation, the cone rod 50 is pulled out of the thrusting unit 202 external guide sleeve receptacle 228 by the ROV 30 and back to the surface. The rod 50 will be monitored as it leaves the thrusting unit 202 by the ROV 30.

At this point, the ROV 30 will need to disconnect from the seabed unit's hot stab receptacle 226 in order to hook up the bale of the seabed unit 10 to the support vessel's 20 winch wire. The ROV 30 will then reconnect the hydraulic connections (i.e., the hot stab receptacle 226) and start pumping water into the suction caisson 102 (via pump 222) to pump the suction caisson 102 out of the soil. The suction caisson 102 is pumped out until it reaches its initial self-embedment depth. The ROV 30 then disconnects the hydraulics (i.e., disengages from the hot stab receptacle 226) and then re-opens the butterfly vent valves 126. The ROV 30 will then observe the suction caisson 102 being pulled out of the soil, with the thrusting unit 202 attached, and the entire seabed unit 10 is lifted to the surface by the support vessel's winch.

Once at the surface, the seabed unit 10 is lifted out of the water using the support vessel's A-Frame and lowered onto the deck. This forms a self-orienting lifting bridle for stern roller retrieval (and launching) of the seabed unit 10. Typically, only six people are allowed on the back deck during the seabed unit's recovery. Those people are the safety supervisor, the ROV supervisor, the winch operator, the vessel A-Frame operator, and the two tag line riggers. Thus the present invention reduces dramatically the number of crewmembers needed to accomplish the soil measurement task.

To finish the recovery cycle, the seabed unit is retrieved by heaving in on the deployment wire. The seabed unit 10 is positioned in the LARS frame and skid rail by moving the support vessel's A-Frame gantry in-board of the stern of the vessel as required. Next, the seabed unit is brought to a position past the breakover point by heaving in on the deployment wire while keeping the LARS wire taunt. The seabed unit is then brought into horizontal position in the LARS frame and the skid rail by simultaneously heaving in on the LARS wire and moving the vessel A-Frame gantry into its stowed position. Finally, the seabed unit 10 is brought into its stowed position by heaving in on the LARS wire while maintaining slack in the deployment wire.

As shown in the foregoing, the seabed unit 10 is designed not to require any elaborate electrical control units, power packs, hydraulic systems and other features—although those features can be added, if necessary, by one skilled in the art with knowledge of this invention.

The present invention, therefore, is well adapted to carry out the objects and attain the ends and advantages mentioned, as well as others inherent therein. While the present invention has been depicted, described, and is defined by reference to particular preferred embodiments of the invention, such references do not imply a limitation on the invention, and no such limitation is to be inferred. The invention is capable of considerable modification, alternation, and equivalents in form and function, as will occur to those ordinarily skilled in the pertinent arts. The depicted and described preferred embodiments of the invention are exemplary only, and are not exhaustive of the scope of the invention. Consequently, the invention is intended to be limited only by the spirit and scope of the appended claims, giving full cognizance to equivalents in all respects.

What is claimed is:

1. The method of measuring seafloor site soil characteristics, said method comprising the steps of:
    (a) providing a caisson, said caisson constructed and arranged for embedment into said seafloor, said caisson further having a thruster;
    (b) lowering said caisson to said site on said seafloor;
    (c) providing a remotely operated vehicle;
    (d) deploying said remotely operated vehicle to said site;
    (e) embedding said caisson into said seafloor with said remotely operated vehicle;
    (f) providing a measuring device;
    (g) lowering said measuring device to said site;
    (h) grasping said measuring device with said remotely operated vehicle;
    (i) mating said measuring device to said thruster;
    (j) inserting said measuring device into said seafloor with said thruster; and
    (k) measuring said soil characteristics of said site of said seafloor.

2. The method of claim 1, wherein said step of inserting said measuring device into said seafloor comprises the steps of:
    (l) said thruster providing at least one jacking actuator, said jacking actuator controlled by said remotely operated vehicle, said jacking actuator capable of extension and retraction;
    (m) providing a lower clamp for said thruster, said lower clamp constructed and arranged to clamp said measuring device when said lower clamp is closed and to release said measuring device when said lower clamp is opened;
    (n) providing an upper clamp for said thruster, said upper clamp constructed and arranged to clamp said measuring device when said upper clamp is closed and to release said measuring device when said upper clamp is opened;
    (p) closing said lower clamp;
    (q) opening said upper clamp;
    (r) extending said jacking actuator to insert said measuring device into said seafloor;
    (s) closing said upper clamp;
    (t) opening said lower clamp;
    (u) retracting said jacking actuator; and
    (v) if said measuring device has not yet reached a desired depth, then repeating said steps (p) to (u) until said measuring device has reached said desired depth.

3. The method of claim 1, said method further comprising the step of recovering said measuring device.

4. The method of claim 3, wherein said step of recovering said measuring device comprises the steps of:
    (1) said thruster providing at least one jacking actuator, said jacking actuator capable of extension and retraction under the control of said remotely operated vehicle;
    (2) providing a lower clamp for said thruster, said lower clamp constructed and arranged to clamp said measuring device when said lower clamp is closed and to release said measuring device when said lower clamp is opened;
    (3) providing an upper clamp for said thruster, said upper clamp constructed and arranged to clamp said measuring device when said upper clamp is closed and to release said measuring device when said upper clamp is opened;
    (4) closing said lower clamp;
    (5) opening said upper clamp;
    (6) retracting said jacking actuator;
    (7) closing said upper clamp;
    (8) opening said lower clamp; and
    (9) if said measuring device has not been recovered, then repeating said steps (4) to (8) until said measuring device has been recovered.

* * * * *